US009040018B2

(12) United States Patent
Alper

(10) Patent No.: US 9,040,018 B2
(45) Date of Patent: May 26, 2015

(54) MONOCLONAL ANTIBODIES AGAINST ALPHA-ACTININ-4 ANTIGENS, AND USES THEREFOR

(76) Inventor: Özge Alper, Bethesda, MD (US)

(*) Notice: Subject to any disclaimer, the term of this patent is extended or adjusted under 35 U.S.C. 154(b) by 0 days.

(21) Appl. No.: 13/976,811

(22) PCT Filed: Dec. 23, 2011

(86) PCT No.: PCT/US2011/067135
§ 371 (c)(1),
(2), (4) Date: Jun. 27, 2013

(87) PCT Pub. No.: WO2012/092175
PCT Pub. Date: Jul. 5, 2012

(65) Prior Publication Data
US 2014/0065064 A1    Mar. 6, 2014

Related U.S. Application Data

(60) Provisional application No. 61/428,159, filed on Dec. 29, 2010, provisional application No. 61/430,874, filed on Jan. 7, 2011.

(51) Int. Cl.
*C07K 16/18* (2006.01)
*G01N 33/574* (2006.01)

(52) U.S. Cl.
CPC .......... *C07K 16/18* (2013.01); *G01N 33/57415* (2013.01); *G01N 2333/4712* (2013.01); *G01N 33/57484* (2013.01)

(58) Field of Classification Search
None
See application file for complete search history.

(56) References Cited

U.S. PATENT DOCUMENTS

| 2004/0219572 A1 | 11/2004 | Chen et al. |
| 2008/0293162 A1 | 11/2008 | Alper |
| 2009/0081248 A1 | 3/2009 | Paterson et al. |
| 2009/0221440 A1 | 9/2009 | Ding et al. |

FOREIGN PATENT DOCUMENTS

WO    WO 2010/057175 A1    5/2010

OTHER PUBLICATIONS

Honda et al. (Journal of Cell Biology, 140(6): 1383-1393, 1998).*
Cho, N.H. et al. (2006), "Comparative proteomics of pulmonary tumors with neuroendocrine differentiation" *J. Proteome Res.*, 5(3):643-650.
Dai et al. (2006), "Identification and analysis of altered α1,6-fucosylated glycoproteins associated with hepatocellular carcinoma metastasis" *Proteomics* 6(21):5857-5867.
Honda et al. (1998). "Actinin-4, a novel actin-bundling protein associated with cell motility and cancer invasion" *J. Cell. Biol.*, 140(6):1383-1393.
International Search Report and Written Opinion issued in International Patent Application No. PCT/US2011/67135, mailed May 4, 2012.

* cited by examiner

*Primary Examiner* — Brad Duffy
*Assistant Examiner* — Nelson B Moseley, II
(74) *Attorney, Agent, or Firm* — Kenealy Vaidya LLP

(57) ABSTRACT

Monoclonal antibodies (MoAbs or mAbs) specific for ALPHA-ACTININ-4 antigens, hybridoma lines that secrete these ALPHA-ACTININ-4 mAbs, and the use of such mAbs to detect ALPHA-ACTININ-4 antigens, particularly those expressed by cancer cells are disclosed. Chimeric and humanized antibodies based upon these anti-ALPHA-ACTININ-4 mAbs, processes for producing monoclonal, chimeric, and humanized antibodies using recombinant DNA technology, and their therapeutic uses, particularly in the treatment of cancer are also disclosed. Methods and kits for the immunodetection and immunotherapy of cells for samples which express ALPHA-ACTININ-4 antigens are additionally disclosed.

22 Claims, 17 Drawing Sheets

| Query | Observed | Mr(expt) | Mr(calc) | Delta | Miss | Score | Expect | Rank | Peptide |
|---|---|---|---|---|---|---|---|---|---|
| 17 | 406.2905 | 810.5664 | 810.4963 | 0.0701 | 0 | 37 | 0.13 | 1 | K.VQQIVPK.R |
| 25 | 432.7799 | 863.5452 | 863.4752 | 0.0700 | 0 | 48 | 0.011 | 1 | K.ALDFIASK.G |
| 27 | 437.7463 | 873.4780 | 873.4192 | 0.0588 | 0 | 14 | 30 | 1 | K.STLPDADR.E |
| 30 | 447.7976 | 893.5806 | 893.5334 | 0.0472 | 0 | 29 | 0.83 | 1 | R.EAILAIHK.E |
| 66 | 387.2115 | 1158.6127 | 1158.5629 | 0.0498 | 1 | 25 | 2.6 | 1 | K.STLPDADRER.E |
| 76 | 607.8419 | 1213.6692 | 1213.5727 | 0.0965 | 0 | 52 | 0.0056 | 1 | K.ASIHEAWTDGK.E |
| 77 | 608.3870 | 1214.7594 | 1214.6659 | 0.0936 | 0 | 65 | 0.00024 | 1 | K.LASDLLEWIR.R |
| 100 | 676.8711 | 1351.7276 | 1351.6190 | 0.1086 | 0 | (74) | 3.2e-05 | 1 | K.GISQEQMQEFR.A |
| 105 | 684.8512 | 1367.6878 | 1367.6140 | 0.0739 | 0 | 77 | 1.7e-05 | 1 | K.GISQEQMQEFR.A + Oxidation (M) |
| 113 | 715.4405 | 1428.8664 | 1428.7572 | 0.1092 | 0 | 63 | 0.00042 | 1 | R.TINEVENQILTR.D |
| 115 | 478.6249 | 1432.8529 | 1432.7133 | 0.1396 | 0 | 29 | 0.92 | 1 | R.LSNRPAFMPSEGK.M |
| 127 | 495.9607 | 1484.6603 | 1484.7524 | 0.1078 | 0 | 8 | 1.3e+02 | 1 | K.NVNVQNFHISWK.D |
| 132 | 754.4214 | 1506.8282 | 1506.6950 | 0.1332 | 0 | 50 | 0.0094 | 1 | K.AGTQIENIDEDFR.D |
| 133 | 757.9631 | 1513.9116 | 1513.7988 | 0.1129 | 0 | 68 | 0.00011 | 1 | K.LVSIGAEEIVDGNAK.M |
| 136 | 769.4519 | 1536.8892 | 1536.7671 | 0.1221 | 0 | 91 | 7e-07 | 1 | R.FAIQDISVEETSAK.E |
| 137 | 769.5112 | 1537.0078 | 1536.7671 | 0.2407 | 0 | (42) | 0.044 | 1 | R.FAIQDISVEETSAK.E |
| 154 | 871.4824 | 1740.9502 | 1740.8054 | 0.1448 | 0 | 107 | 1.9e-08 | 1 | R.ETTDTDTADQVIASFK.V |
| 158 | 897.0067 | 1791.9988 | 1791.8502 | 0.1487 | 0 | 89 | 1e-06 | 1 | R.MAPYQGPDAVPGALDYK.S |
| 160 | 904.9987 | 1807.9828 | 1807.8451 | 0.1378 | 0 | (32) | 0.62 | 1 | R.MAPYQGPDAVPGALDYK.S + Oxidation (M) |
| 167 | 640.7231 | 1919.1475 | 1919.0000 | 0.1475 | 0 | (37) | 0.16 | 1 | K.LSGSNPYTTVTPQIINSK.W |
| 168 | 960.5824 | 1919.1502 | 1919.0000 | 0.1502 | 0 | 107 | 1.6e-08 | 1 | K.LSGSNPYTTVTPQIINSK.W |
| 169 | 667.0397 | 1998.0973 | 1997.9265 | 0.1708 | 0 | 62 | 0.00063 | 1 | K.MVSDINNGWQHLEQQAEK.G |
| 171 | 687.7030 | 2060.0872 | 2059.9520 | 0.1351 | 0 | 81 | 7.3e-06 | 1 | K.VLAVNQENEHLMEDYEK.L |

FIG. 1

OVERALL SURVIVAL RATE OF BREAST CANCER PATIENTS WITH ACTININ-4 EXPRESSION IS SIGNIFICANTLY HIGHER THAN PATIENTS WITH NEGATIVE ACTININ-4 EXPRESSION

Amino Acid Sequence of Alper-ALPHA-ACTININ-4 mAb Heavy Chain (SEQ ID NO. 1)

```
|----------FWR1----------|
L  E  E  S  G  G  G  G  L  V  K  P  G  G  S  L  K  L  S  C  A
                                              |------CDR1------>
A  S  G  F  T  F  S  S  Y  A  M  S  W  V  R  Q  T  P  E  K  R  L  E  W
                        <-----CDR1-----|  |---------FWR2---------|
                                                       |---------CDR2--------->
V  A  S  I  S  S  G  G  S  T  Y  Y  P  D  S  V  K  G  R  F
<---|                                          <----CDR2----|
|-----------------FWR3-----------------
T  I  S  R  D  N  A  R  N  I  L  Y  L  Q  M  S  S  L  R  S  E  D  T
-----------------FWR3-----------------|
                                                         |------CDR3------>
A  M  Y  Y  C  A  R  E  L  G  R  K  G  Y  F  D  V  W  G  Q  G  T  T  V
                 <----CDR3----|
```

FIG. 4

Amino Acid Sequence of Alper-ALPHA-ACTININ-4 mAb Light Chain (SEQ ID NO. 5)

```
<-----------------------FWR1----------------------->
D I L M T Q S P T T M A A S P G E K I T I T C
                                <----------CDR1---------->
S A S S S I S S         N Y L H         W Y Q Q K P G F S
                                                <---FWR2--->
<---CDR2--->
P K L L I Y         R T S N L A S         G V P A R F S G S G
<--------------------FWR3-------------------->
S G T S Y S L T I G T M E A E D V A T Y Y C
<---------CDR3--------->
Q G S S I P R T F G S G T K L E I K
```

FIG. 5 k3n H-Chain
BLASTN 2.2.20 [Feb-08-2009]

Database: igallncseq 530 sequences; 154,952 total letters

Query=tmpseq_0 (1276 letters)

Sequences producing significant alignments:

```
                                          Score      E
                                         (bits)    Value
IGHV3-h*01                                 310     7e-86
IGHV3-48*01                                308     2e-85
IGHV3-*02                                  307     6e-85
IGHV3-48*02                                305     2e-84
IGHV3-23*04                                305     2e-84
IGHV3-21*02                                305     2e-84
IGHV3-21*01                                305     2e-84
IGHV3-48*03                                302     1e-83
IGHV3-23*01                                302     1e-83
IGHV3-11*01                                302     1e-83
```

Domain classification requested: Kabat and IMGT/V-QUEST system

| ID% | tmpseq_0 | Sequence |
|---|---|---|
| | | L E E S G G G L V K P G G S L K L S C A |
| | | CTGGAGGAGTCTGGGGGAGGCTTAGTGAAGCCTGGAGGGTCCCTGAAACTCTCCTGTGCAG |
| | | E V Q L V E S G G G L V K P G G S L R L S C A |
| 84.9 (241/284) | IGHV3-h*01 | GAGGTGCAG..............................G......G........ |
| 85.0 (244/287) | IGHV3-48*01 | ----------.T.........................G.A......G........ |
| 84.5 (240/284) | IGHV3-h*02 | ----------.T.........................G.AC.....G........ |
| 90.0 (9/10) | IGHD1-20*01 | ----------............................G.A......G........ |
| 90.0 (9/10) | IGHD1-1*01 | ---------------------------------------------------------- |
| 100 (7/7) | IGHD7-27*01 | ---------------------------------------------------------- |
| 88.6 (31/35) | IGHJ6*03 | ---------------------------------------------------------- |
| 96.6 (28/29) | IGHJ6*02 | ---------------------------------------------------------- |
| 84.7 (243/287) | IGHV3-48*02 | ----------.T.........................G.AC.....G........ |
| 84.7 (243/287) | IGHV3-23*04 | ----------.T.........................G.AC.....G........ |
| 84.7 (243/287) | IGHV3-21*02 | ----------.T.........................C.G.C....G........ |
| 84.7 (243/287) | IGHV3-21*01 | ----------.T.........................C.G.C....G........ |
| 84.6 (241/285) | IGHV3-48*03 | ----------.T.........................G.AC.....G........ |
| 84.3 (242/287) | IGHV3-23*01 | ----------.TT........................G.AC.....G........ |
| 84.3 (242/287) | IGHV3-11*01 | ----------.T.........................G.C......G........ |

```
                                                                              <--------------------CDR3------------------>
                         A  M  Y  Y  C              A  R  E  L  G  R  K  G  Y  F  D  V  W  G  Q  G  T  T  V
ID%                      CCATGTATTACTGTG            CAAGAGAACTGGGACGTAAGGGGTACTTCGATTCTGGGCCAAGGGACCACGGT    362
              tmpseq_0   A  V  Y  Y  C              A  R                                                    293
84.9(241/284) IGHV3-h*01  .TG...........  .......   .G..........                                             272
85.0(244/287) IGHV3-48*01 .TG...........  .......   .G..........                                             275
84.5(240/284) IGHV3-h*02  .TG.T.........  .......   .G..........                                             272
90.0(9/10)    IGHD1-20*01 --------------  -------   ---------A..                                              6
90.0(9/10)    IGHD1-1*01  --------------  -------   ---------A..                                              6
100(7/7)      IGHD7-27*01 --------------  -------   ........                                                  3
88.6(31/35)   IGHJ6*03    --------------  -------   -----------------........A.G.C............A..            18
96.6(28/29)   IGHJ6*02    --------------  -------   -----------------.........C...............               24
84.7(243/287) IGHV3-48*02 .TG...........  .......   .G..........                                             275
84.7(243/287) IGHV3-23*04 ..G.A.........  .......   .G.A........                                             275
84.7(243/287) IGHV3-21*02 .TG...........  .......   .G..........                                             275
84.7(243/287) IGHV3-21*01 .TG...........  .......   .G..........                                             275
84.6(241/285) IGHV3-48*03 .TG.T.........  .......   .G..........                                             275
84.3(242/287) IGHV3-23*01 ..G.A.........  .......   .G.A........                                             275
84.3(242/287) IGHV3-11*01 ..G...........  .......   .G..........                                             275
```

```
K3n Kappa-Chain
BLASTN 2.2.20 [Feb-08-2009]
Database: igallncseq 530 sequences; 154,952 total letters
Query= tmpseq_0  (1209 letters)

Sequences producing significant alignments:         Score    E
                                                    (bits)   Value
IGKV1D-37*01                                        190      8e-50
IGKV1-37*01                                         190      8e-50
IGKV1-27*01                                         185      2e-48
IGKV1D-39*01                                        184      6e-48
IGKV1-39*01                                         184      6e-48
IGKV1-5*01                                          182      2e-47
IGKV7-3*01                                          182      2e-47
IGKV1-5*03                                          182      2e-47
IGKV1-NL1*01                                        181      5e-47
IGKV1/OR2-108*01                                    179      2e-46

Domain classification requested: Kabat system
```

| ID% | tmpseq_0 | | | | | | | |
|---|---|---|---|---|---|---|---|---|
| | | <----------CDR1---------->  | | | N Y L H | <-------- | -----FWR2 | |
| | | S A S S S I S S | | | | W Y Q Q K P G F S | |
| | 96 | GTGCCAGCTCAAGTATAAGTTCC------ | | | AATTACTTGCAT | TGGTATCAGCAGAAGCCAGGATTCTC | 156 |
| | | R V S Q G I S | | | S Y L N | W Y R Q K P G K V | |
| 73.2(197/269) | IGKV1D-37*01 | 71 | .G.TG..TCAGG.C..T.. | ------ | .G...T..AA.. | ...G......A.......GAAAGT | 128 |
| 73.2(197/269) | IGKV1-37*01 | 71 | .G.TG..TCAGG.C..T.. | ------ | .G...T..AA.. | ...G......A.......GAAAGT | 128 |
| 71.6(202/282) | IGKV1-27*01 | 71 | .G..G..TCAGG.C..T.. | ------ | ...T..AGCC | ..........A.......GAAAGT | 128 |
| 82.4(28/34) | IGKJ1*01 | | | | | | |
| 80.0(28/35) | IGKJ4*02 | | | | | | |
| 71.4(202/283) | IGKV1D-39*01 | 71 | .G..A..TCAG..C..T.. | ------ | .GC..T..AA.. | ..........A.......GAAAG. | 128 |
| 71.4(202/283) | IGKV1-39*01 | 71 | .G..A..TCAG..C..T.. | ------ | .GC..T..AA.. | ..........A.......GAAAG. | 128 |
| 71.3(201/282) | IGKV1-5*01 | 71 | .G......TCAG.....T.. | AG... | ...GG...GCC | ..........A.......GAAAG. | 128 |
| 71.0(203/286) | IGKV7-3*01 | 71 | .A......TGAG...G.C...T. | TTGGGAATA..C.TAA.T..C | | ..........A.......CAAC. | 140 |
| 71.3(201/282) | IGKV1-5*03 | 71 | .G......TCAG.....T.. | AG... | ...GG...GCC | ..........A.......GAAAG. | 128 |
| 71.0(201/283) | IGKV1-NL1*01 | 71 | .G..G..TCAGG.C..T.. | ------ | ...CT..AGCC | ..........A.......GAAAG. | 128 |
| 70.5(203/288) | IGKV1/OR2-108*01 | 71 | .G..A..TCAGG.C..T.. | ------ | ...GGG..ATCC | ..........A.......GCAAG. | 128 |

```
                                   ----------CDR3------->
ID%            tmpseq_0         Q  G  S  S  I  P  R  T  F  G  S  G  T  K  L  E  I  K
               297  AGGGTAGTAGTATACCACGCCACGTTCGGCTCGGGGACAAAGTTGGAAATAAAAC  350

73.2(197/269)  IGKV1D-37*01      269  ------------------------------------------------------  279
73.2(197/269)  IGKV1-37*01       269  ------------------------------------------------------  279
71.6(202/282)  IGKV1-27*01       269  ..TA..AC..............................................  38
82.4(28/34)    IGKJ1*01            5  ......................CAA.....G.......C...............  38
80.0(28/35)    IGKJ4*02            4  ......................GGA.....G....G..C...............  38
71.4(202/283)  IGKV1D-39*01      269  ..A..TAC..............................................  280
71.4(202/283)  IGKV1-39*01       269  ..A..TAC..............................................  280
71.3(201/282)  IGKV1-5*01        269  ..TA..A...............................................  279
71.0(203/286)  IGKV7-3*01        281  ..A.....A.............................................  286
71.3(201/282)  IGKV1-5*03        269  ..TA..A...............................................  279
71.0(201/283)  IGKV1-NL1*01      269  ..TA.TA...............................................  280
70.5(203/288)  IGKV1/OR2-108*01  269  ..A.TA..C..CC.........................................  285
```

FIG. 7F

SEQUENCE LISTING

```
<160> NUMBER OF SEQ ID NOS: 81

<210> SEQ ID NO 1
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Leu Glu Glu Ser Gly Gly Gly Leu Val Lys Pro Gly Gly Ser Leu Lys
1               5                   10                  15

Leu Ser Cys Ala Ala Ser Gly Phe Thr Phe Ser Ser Tyr Ala Met Ser
            20                  25                  30

Trp Val Arg Gln Thr Pro Glu Lys Arg Leu Glu Trp Val Ala Ser Ile
        35                  40                  45

Ser Ser Gly Gly Ser Thr Tyr Tyr Pro Asp Ser Val Lys Gly Arg Phe
    50                  55                  60

Thr Ile Ser Arg Asp Asn Ala Arg Asn Ile Leu Tyr Leu Gln Met Ser
65                  70                  75                  80

Ser Leu Arg Ser Glu Asp Thr Ala Met Tyr Tyr Cys Ala Arg Glu Leu
                85                  90                  95

Gly Arg Lys Gly Tyr Phe Asp Val Trp Gly Gln Gly Thr Thr Val
            100                 105                 110

<210> SEQ ID NO 2
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 2

Ser Tyr Ala Met Ser
1               5

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Ile Ser Ser Gly Gly Ser Thr Tyr Tyr Pro Asp Ser Val Lys Gly
1               5                  10                  15

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Arg Glu Leu Gly Arg Lys Gly Tyr Phe Asp Val
1               5                   10

<210> SEQ ID NO 5
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Leu Met Thr Gln Ser Pro Thr Thr Met Ala Ala Ser Pro Gly
1               5                   10                  15

Glu Lys Ile Thr Ile Thr Cys Ser Ala Ser Ser Ile Ser Ser Asn
            20                  25                  30

Tyr Leu His Trp Tyr Gln Gln Lys Pro Gly Phe Ser Pro Lys Leu Leu
            35                  40                  45

Ile Tyr Arg Thr Ser Asn Leu Ala Ser Gly Val Pro Ala Arg Phe Ser
        50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Arg Thr Phe Gly Ser Gly Thr Lys Leu Glu Ile Lys
            100                 105

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6
```

```
Ser Ala Ser Ser Ser Ile Ser Ser Asn Tyr Leu His
1               5                  10
```

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Arg Thr Ser Asn Leu Ala Ser
1               5
```

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Gln Gln Gly Ser Ser Ile Pro Arg Thr
1               5
```

<210> SEQ ID NO 9
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(333)
<220> FEATURE:
<221> NAME/KEY: modified_base
<222> LOCATION: (333)..(333)
<223> OTHER INFORMATION: a, c, t or g

<400> SEQUENCE: 9

```
ctg gag gag tct ggg gga ggc tta gtg aag cct ggg ggg tcc ctg aaa       48
Leu Glu Glu Ser Gly Gly Gly Leu Val Lys Pro Gly Gly Ser Leu Lys
1               5                   10                  15 ctc tcc tgt gca gcc tct gga ttc act ttc agt agc tat gcc atg tct       96
Leu Ser Cys Ala Ala Ser Gly Phe Thr Phe Ser Ser Tyr Ala Met Ser
            20                  25                  30 tgg gtt cgc cag act cca gag aag agg ctg gag tgg gtc gca tcc att      144
Trp Val Arg Gln Thr Pro Glu Lys Arg Leu Glu Trp Val Ala Ser Ile
        35                  40                  45 agt agt ggt ggt agc acc tac tat cca gac agt gtg aag ggc cga ttc      192
Ser Ser Gly Gly Ser Thr Tyr Tyr Pro Asp Ser Val Lys Gly Arg Phe
    50                  55                  60 acc atc tcc aga gat aat gcc agg aac atc ctg tac ctg caa atg agc      240
Thr Ile Ser Arg Asp Asn Ala Arg Asn Ile Leu Tyr Leu Gln Met Ser
65                  70                  75                  80 agt ctg agg tct gag gac acg gcc atg tat tac tgt gca aga gaa ctg      288
Ser Leu Arg Ser Glu Asp Thr Ala Met Tyr Tyr Cys Ala Arg Glu Leu
                85                  90                  95 gga cgt aag ggg tac ttc gat gtc tgg ggc caa ggg acc acg gtn          333
Gly Arg Lys Gly Tyr Phe Asp Val Trp Gly Gln Gly Thr Thr Val
            100                 105                 110
```

<210> SEQ ID NO 10
<211> LENGTH: 325
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(324)

<400> SEQUENCE: 10

```
gac att ctg atg acc cag tct cca acc acc atg gct gca tct ccc ggg        48
Asp Ile Leu Met Thr Gln Ser Pro Thr Thr Met Ala Ala Ser Pro Gly
1               5                   10                  15 gag aag atc act atc acc tgc agt gcc agc tca agt ata agt tcc aat        96
Glu Lys Ile Thr Ile Thr Cys Ser Ala Ser Ser Ser Ile Ser Ser Asn
            20                  25                  30 tac ttg cat tgg tat cag cag aag cca gga ttc tcc cct aaa ctc ttg       144
Tyr Leu His Trp Tyr Gln Gln Lys Pro Gly Phe Ser Pro Lys Leu Leu
        35                  40                  45 att tat agg aca tcc aat ctg gct tct gga gtc cca gct cgc ttc agt       192
Ile Tyr Arg Thr Ser Asn Leu Ala Ser Gly Val Pro Ala Arg Phe Ser
    50                  55                  60 ggc agt ggg tct ggg acc tct tac tct ctc aca att ggc acc atg gag       240
Gly Ser Gly Ser Gly Thr Ser Tyr Ser Leu Thr Ile Gly Thr Met Glu
65                  70                  75                  80 gct gaa gat gtt gcc act tac tac tgc cag cag ggt agt agt ata cca       288
Ala Glu Asp Val Ala Thr Tyr Tyr Cys Gln Gln Gly Ser Ser Ile Pro
                85                  90                  95 cgc acg ttc ggc tcg ggg aca aag ttg gaa ata aaa c                     325
Arg Thr Phe Gly Ser Gly Thr Lys Leu Glu Ile Lys
            100                 105
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Val Gln Gln Leu Val Pro Lys
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Ala Leu Asp Phe Ile Ala Ser Lys
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

```
Ser Thr Leu Pro Asp Ala Asp Arg
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Ala Ile Leu Ala Ile His Lys
1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Thr Leu Pro Asp Ala Asp Arg Glu Arg
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Ser Ile His Glu Ala Trp Thr Asp Gly Lys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Ala Ser Asp Leu Leu Glu Trp Ile Arg
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ile Ser Gln Glu Gln Met Gln Glu Phe Arg
1               5                   10

<210> SEQ ID NO 19
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 19

Thr Ile Asn Glu Val Glu Asn Gln Ile Leu Thr Arg
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Ser Asn Arg Pro Ala Phe Met Pro Ser Glu Gly Lys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asn Val Asn Val Gln Asn Phe His Ile Ser Trp Lys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Gly Thr Gln Ile Glu Asn Ile Asp Glu Asp Phe Arg
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Val Ser Ile Gly Ala Glu Glu Ile Val Asp Gly Asn Ala Lys
1               5                   10                  15

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Ala Ile Gln Asp Ile Ser Val Glu Glu Thr Ser Ala Lys
1               5                   10
```

```
<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Thr Thr Asp Thr Asp Thr Ala Asp Gln Val Ile Ala Ser Phe Lys
1               5                   10                  15

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Met Ala Pro Tyr Gln Gly Pro Asp Ala Val Pro Gly Ala Leu Asp Tyr
1               5                   10                  15

Lys

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Ser Gly Ser Asn Pro Tyr Thr Thr Val Thr Pro Gln Ile Ile Asn
1               5                   10                  15

Ser Lys

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Met Val Ser Asp Ile Asn Asn Gly Trp Gln His Leu Glu Gln Ala Glu
1               5                   10                  15

Lys

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Leu Ala Val Asn Gln Glu Asn Glu His Leu Met Glu Asp Tyr Glu
1               5                   10                  15

Lys
```

```
<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Val Gln Gln Leu Val Pro Lys Arg
1               5

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Ala Leu Asp Phe Ile Ala Ser Lys Gly
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Ser Thr Leu Pro Asp Ala Asp Arg Glu
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Glu Ala Ile Leu Ala Ile His Lys Glu
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Ser Thr Leu Pro Asp Ala Asp Arg Glu Arg Glu
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35
```

```
Lys Ala Ser Ile His Glu Ala Trp Thr Asp Gly Lys Glu
1               5                  10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Leu Ala Ser Asp Leu Leu Glu Trp Ile Arg Arg
1               5                  10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Gly Ile Ser Gln Glu Gln Met Gln Glu Phe Arg Ala
1               5                  10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Oxidized-Met

<400> SEQUENCE: 38

Lys Gly Ile Ser Gln Glu Gln Met Gln Glu Phe Arg Ala
1               5                  10

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Thr Ile Asn Glu Val Glu Asp Gln Ile Leu Thr Arg Asp
1               5                  10

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Leu Ser Asn Arg Pro Ala Phe Met Pro Ser Glu Gly Lys Met
1               5                  10                  15
```

```
<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Asn Val Asn Val Gln Asn Phe His Ile Ser Trp Lys Asp
1               5                   10

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Ala Gly Thr Gln Ile Glu Asn Ile Asp Glu Asp Phe Arg Asp
1               5                   10                  15

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Leu Val Ser Ile Gly Ala Glu Glu Ile Val Asp Gly Asn Ala Lys
1               5                   10                  15

Met

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Phe Ala Ile Gln Asp Ile Ser Val Glu Glu Thr Ser Ala Lys Glu
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Phe Ala Ile Gln Asp Ile Ser Val Glu Glu Thr Ser Ala Lys Glu
1               5                   10                  15

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 46

Arg Glu Thr Thr Asp Thr Asp Thr Ala Asp Gln Val Ile Ala Ser Phe
1               5                   10                  15

Lys Val

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Met Ala Pro Tyr Gln Gly Pro Asp Ala Val Pro Gly Ala Leu Asp
1               5                   10                  15

Tyr Lys Ser

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Oxidized-Met

<400> SEQUENCE: 48

Arg Met Ala Pro Tyr Gln Gly Pro Asp Ala Val Pro Gly Ala Leu Asp
1               5                   10                  15

Tyr Lys Ser

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Leu Ser Gly Ser Asn Pro Tyr Thr Thr Val Thr Pro Gln Ile Ile
1               5                   10                  15

Asn Ser Lys Trp
            20

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Leu Ser Gly Ser Asn Pro Tyr Thr Thr Val Thr Pro Gln Ile Ile
1               5                   10                  15

Asn Ser Lys Trp
            20
```

```
<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Met Val Ser Asp Ile Asn Asn Gly Trp Gln His Leu Glu Gln Ala
1               5                   10                  15

Glu Lys Gly

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Val Leu Ala Val Asn Gln Glu Asn Glu His Leu Met Glu Asp Tyr
1               5                   10                  15

Glu Lys Leu

<210> SEQ ID NO 53
<211> LENGTH: 293
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(291)

<400> SEQUENCE: 53 gag gtg cag ctg gtg gag tct ggg gga ggc ttg gta aag cct ggg ggg       48
Glu Val Gln Leu Val Glu Ser Gly Gly Gly Leu Val Lys Pro Gly Gly
1               5                   10                  15 tcc ctg aga ctc tcc tgt gca gcc tct gga ttc acc ttc agt gac tac       96
Ser Leu Arg Leu Ser Cys Ala Ala Ser Gly Phe Thr Phe Ser Asp Tyr
            20                  25                  30 tac atg aac tgg gtc cgc cag gct cca ggg aag ggg ctg gag tgg gtc      144
Tyr Met Asn Trp Val Arg Gln Ala Pro Gly Lys Gly Leu Glu Trp Val
        35                  40                  45 tca tcc att agt agt agt agt acc ata tac tac gca gac tct gtg aag      192
Ser Ser Ile Ser Ser Ser Ser Thr Ile Tyr Tyr Ala Asp Ser Val Lys
    50                  55                  60 ggc cga ttc acc atc tcc aga gac aac gcc aag aac tca ctg tat ctg      240
Gly Arg Phe Thr Ile Ser Arg Asp Asn Ala Lys Asn Ser Leu Tyr Leu
65                  70                  75                  80 caa atg aac agc ctg aga gcc gag gac acg gct gtg tat tac tgt gcg      288
Gln Met Asn Ser Leu Arg Ala Glu Asp Thr Ala Val Tyr Tyr Cys Ala
                85                  90                  95 aga ga                                                               293
Arg

<210> SEQ ID NO 54
<211> LENGTH: 97
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 54

| Glu | Val | Gln | Leu | Val | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Asp | Tyr |
|---|---|---|---|---|---|---|---|---|---|---|---|---|---|---|---|
| | | | 20 | | | | | 25 | | | | | 30 | | |

| Tyr | Met | Asn | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Ser | Ile | Ser | Ser | Ser | Ser | Thr | Ile | Tyr | Tyr | Ala | Asp | Ser | Val | Lys |
|---|---|---|---|---|---|---|---|---|---|---|---|---|---|---|---|
| 50 | | | | | 55 | | | | | 60 | | | | | |

| Gly | Arg | Phe | Thr | Ile | Ser | Arg | Asp | Asn | Ala | Lys | Asn | Ser | Leu | Tyr | Leu |
|---|---|---|---|---|---|---|---|---|---|---|---|---|---|---|---|
| 65 | | | | 70 | | | | | 75 | | | | | 80 | |

| Gln | Met | Asn | Ser | Leu | Arg | Ala | Glu | Asp | Thr | Ala | Val | Tyr | Tyr | Cys | Ala |
|---|---|---|---|---|---|---|---|---|---|---|---|---|---|---|---|
| | | | 85 | | | | | 90 | | | | | 95 | | |

Arg

<210> SEQ ID NO 55
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
ctggtggagt ctgggggagg cttggtacag cctgggggt ccctgagact ctcctgtgca       60
gcctctggat tcaccttcag tagctatagc atgaactggg tccgccaggc tccagggaag     120
gggctggagt gggttttcata cattagtagt agtagtagta ccatatacta cgcagactct    180
gtgaagggcc gattcaccat ctccagagac aatgccaaga actcactgta tctgcaaatg     240
aacagcctga gagccgagga cacggctgtg tattactgtg cgagaga                   287

<210> SEQ ID NO 56
<211> LENGTH: 284
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
ctggtggagt ctgggggagg cttggtaaag cctgggggt ccctgagact ctcctgtgca       60
gcctctggat tcaccttcag tgactactac atgaactggg tccgccaggc tccagggaag     120
gggctggagt gggtctcatc cattagtagt agtagtacca tatactacgc agactctgtg     180
aagggccgat tcaccatctc cagagacaac gccaagaact cactgtatct gcaaatgaac    240
agcctgagag ccgaggacac ggctgtttat tactgtgcga gaga                      284

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aactggaacg                                                             10

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
aactggaacg                                                              10

<210> SEQ ID NO 59
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tacatggacg tctggggcaa agggaccacg gt                                     32

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gacgtctggg gccaagggac cacggt                                            26

<210> SEQ ID NO 61
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
ctggtggagt ctgggggagg cttggtacag cctggggggt ccctgagact ctcctgtgca       60
gcctctggat tcaccttcag tagctatagc atgaactggg tccgccaggc tccagggaag      120
gggctggagt gggtttcata cattagtagt agtagtagta ccatatacta cgcagactct      180
gtgaagggcc gattcaccat ctccagagac aatgccaaga actcactgta tctgcaaatg      240
aacagcctga gagacgagga cacggctgtg tattactgtg cgagaga                    287

<210> SEQ ID NO 62
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
ctggtggagt ctgggggagg cttggtacag cctggggggt ccctgagact ctcctgtgca       60
gcctctggat tcacctttag cagctatgcc atgagctggg tccgccaggc tccagggaag      120
gggctggagt gggtctcagc tattagtggt agtggtggta gcacatacta cgcagactcc      180
gtgaagggcc ggttcaccat ctccagagac aattccaaga acacgctgta tctgcaaatg      240
aacagcctga gagccgagga cacggccgta tattactgtg cgaaaga         287

<210> SEQ ID NO 63
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
ctggtggagt ctgggggagg cctggtcaag cctggggggt ccctgagact ctcctgtgca    60
gcctctggat tcaccttcag tagctatagc atgaactggg tccgccaggc tccagggaag   120
gggctggagt gggtctcatc cattagtagt agtagtagtt acatatacta cgcagactca   180
gtgaagggcc gattcaccat ctccagagac aacgccaaga actcactgta tctgcaaatg   240
aacagcctga gagccgagga cacggctgtg tattactgtg cgagaga              287

<210> SEQ ID NO 64
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
ctggtggagt ctgggggagg cctggtcaag cctggggggt ccctgagact ctcctgtgca    60
gcctctggat tcaccttcag tagctatagc atgaactggg tccgccaggc tccagggaag   120
gggctggagt gggtctcatc cattagtagt agtagtagtt acatatacta cgcagactca   180
gtgaagggcc gattcaccat ctccagagac aacgccaaga actcactgta tctgcaaatg   240
aacagcctga gagccgagga cacggctgtg tattactgtg cgagaga              287

<210> SEQ ID NO 65
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
ctggtggagt ctgggggagg cttggtacag cctggagggt ccctgagact ctcctgtgca    60
gcctctggat tcaccttcag tagttatgaa atgaactggg tccgccaggc tccagggaag   120
gggctggagt gggtttcata cattagtagt agtggtagta ccatatacta cgcagactct   180
gtgaagggcc gattcaccat ctccagagac aacgccaaga actcactgta tctgcaaatg   240
aacagcctga gagccgagga cacggctgtt tattactgtg cgaga                285

<210> SEQ ID NO 66
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
ctgttggagt ctgggggagg cttggtacag cctggggggt ccctgagact ctcctgtgca    60
gcctctggat tcaccttttag cagctatgcc atgagctggg tccgccaggc tccagggaag   120

```
gggctggagt gggtctcagc tattagtggt agtggtggta gcacatacta cgcagactcc    180
gtgaagggcc ggttcaccat ctccagagac aattccaaga acacgctgta tctgcaaatg    240
aacagcctga gagccgagga cacggccgta tattactgtg cgaaaga                  287
```

<210> SEQ ID NO 67
<211> LENGTH: 287
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
ctggtggagt ctggggggagg cttggtcaag cctggagggt ccctgagact ctcctgtgca    60
gcctctggat tcaccttcag tgactactac atgagctgga tccgccaggc tccagggaag   120
gggctggagt gggtttcata cattagtagt agtggtagta ccatatacta cgcagactct   180
gtgaagggcc gattcaccat ctccagggac aacgccaaga actcactgta tctgcaaatg   240
aacagcctga gagccgagga cacggccgtg tattactgtg cgagaga                  287
```

<210> SEQ ID NO 68
<211> LENGTH: 266
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(264)

<400> SEQUENCE: 68

```
gac atc cag ttg acc cag tct cca tcc tcc ctg tct gca tct gta gga         48
Asp Ile Gln Leu Thr Gln Ser Pro Ser Ser Leu Ser Ala Ser Val Gly
1               5                   10                  15 gac aga gtc acc atc act tgc cgg gtg agt cag ggc att agc agt tat         96
Asp Arg Val Thr Ile Thr Cys Arg Val Ser Gln Gly Ile Ser Ser Tyr
            20                  25                  30 tta aat tgg tat cgg cag aaa cca ggg aaa gtt cct aag ctc ctg atc        144
Leu Asn Trp Tyr Arg Gln Lys Pro Gly Lys Val Pro Lys Leu Leu Ile
        35                  40                  45 tat agt gca tcc aat ttg caa tct gga gtc cca tct cgg ttc agt ggc        192
Tyr Ser Ala Ser Asn Leu Gln Ser Gly Val Pro Ser Arg Phe Ser Gly
    50                  55                  60 agt gga tct ggg aca gat ttc act ctc act atc agc agc ctg cag cct        240
Ser Gly Ser Gly Thr Asp Phe Thr Leu Thr Ile Ser Ser Leu Gln Pro
65                  70                  75                  80 gaa gat gtt gca act tat tac ggt ca                                     266
Glu Asp Val Ala Thr Tyr Tyr Gly
                85
```

<210> SEQ ID NO 69
<211> LENGTH: 88
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Asp Ile Gln Leu Thr Gln Ser Pro Ser Ser Leu Ser Ala Ser Val Gly
1               5                   10                  15

Asp Arg Val Thr Ile Thr Cys Arg Val Ser Gln Gly Ile Ser Ser Tyr
```

```
                  20                  25                  30
Leu Asn Trp Tyr Arg Gln Lys Pro Gly Lys Val Pro Lys Leu Leu Ile
            35                  40                  45

Tyr Ser Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Gly
                85

<210> SEQ ID NO 70
<211> LENGTH: 266
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
gacatccagt tgacccagtc tccatcctcc ctgtctgcat ctgtaggaga cagagtcacc      60
atcacttgcc gggtgagtca gggcattagc agttatttaa attggtatcg cagaaaacca     120
gggaaagttc ctaagctcct gatctatagt gcatccaatt tgcaatctgg agtcccatct     180
cggttcagtg gcagtggatc tgggacagat ttcactctca ctatcagcag cctgcagcct     240
gaagatgttg caacttatta cggtca                                          266

<210> SEQ ID NO 71
<211> LENGTH: 279
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gacatccaga tgacccagtc tccatcctcc ctgtctgcat ctgtaggaga cagagtcacc      60
atcacttgcc gggcgagtca gggcattagc aattatttag cctggtatca gcagaaacca    120
gggaaagttc ctaagctcct gatctatgct gcatccactt tgcaatcagg ggtcccatct    180
cggttcagtg gcagtggatc tgggacagat ttcactctca ccatcagcag cctgcagcct    240
gaagatgttg caacttatta ctgtcaaaag tataacagt                           279

<210> SEQ ID NO 72
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
acgttcggcc aagggaccaa ggtggaaatc aaac                                  34

<210> SEQ ID NO 73
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
```

```
cacgttcggc ggagggacca aggtggagat caaac                              35
```

<210> SEQ ID NO 74
<211> LENGTH: 280
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta                         280
```

<210> SEQ ID NO 75
<211> LENGTH: 280
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta                         280
```

<210> SEQ ID NO 76
<211> LENGTH: 279
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctatgat gcctccagtt tggaaagtgg ggtcccatca   180
aggttcagcg gcagtggatc tgggacagaa ttcactctca ccatcagcag cctgcagcct   240
gatgattttg caacttatta ctgccaacag tataatagt                          279
```

<210> SEQ ID NO 77
<211> LENGTH: 286
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
gacattgtgc tgacccagtc tccagcctcc ttggccgtgt ctccaggaca gagggccacc    60
```

```
atcacctgca gagccagtga gagtgtcagt ttcttgggaa taaacttaat tcactggtat      120
cagcagaaac caggacaacc tcctaaactc ctgatttacc aagcatccaa taaagacact      180
ggggtcccag ccaggttcag cggcagtggg tctgggaccg atttcaccct cacaattaat      240
cctgtggaag ctaatgatac tgcaaattat tactgtctgc agagta                    286
```

```
<210> SEQ ID NO 78
<211> LENGTH: 279
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
```

```
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagt                             279
```

```
<210> SEQ ID NO 79
<211> LENGTH: 280
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
```

```
gacatccaga tgacccagtc tccatcctcc ctgtctgcat ctgtaggaga cagagtcacc      60
atcacttgcc gggcgagtca gggcattagc aattctttag cctggtatca gcagaaacca     120
gggaaagccc ctaagctcct gctctatgct gcatccagat tggaaagtgg ggtcccatcc     180
aggttcagtg gcagtggatc tgggacggat tacactctca ccatcagcag cctgcagcct     240
gaagattttg caacttatta ctgtcaacag tattatagta                            280
```

```
<210> SEQ ID NO 80
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
```

```
gacatccagg tgacccagtc tccatcttcc ctgtctgcgt ctgtaggaga cagagtcacc      60
atcacctgcc gggcaagtca gggcattagc aatgggttat cctggtatca gcagaaacca     120
gggcaagccc ctacgctcct gatctatgct gcatccagtt tgcagtcggg ggtcccatct     180
cggttcagtg gcagtggatc tgggacagat ttcactctca ccatcagcag cctgcagcct     240
gaagatgttg caacttatta ctgtctacag gattatacta cccca                     285
```

```
<210> SEQ ID NO 81
<211> LENGTH: 911
<212> TYPE: PRT
<213> ORGANISM: Homo sapiens
<220> FEATURE:
<223> OTHER INFORMATION: alfa-actinin-4
```

```
<400> SEQUENCE: 81

Met Val Asp Tyr His Ala Ala Asn Gln Ser Tyr Gln Tyr Gly Pro Ser
1               5                   10                  15

Ser Ala Gly Asn Gly Ala Gly Gly Gly Ser Met Gly Asp Tyr Met
            20                  25                  30

Ala Gln Glu Asp Asp Trp Asp Arg Asp Leu Leu Leu Asp Pro Ala Trp
        35                  40                  45

Glu Lys Gln Gln Arg Lys Thr Phe Thr Ala Trp Cys Asn Ser His Leu
    50                  55                  60

Arg Lys Ala Gly Thr Gln Ile Glu Asn Ile Asp Glu Asp Phe Arg Asp
65                  70                  75                  80

Gly Leu Lys Leu Met Leu Leu Leu Glu Val Ile Ser Gly Glu Arg Leu
                85                  90                  95

Pro Lys Pro Glu Arg Gly Lys Met Arg Val His Lys Ile Asn Asn Val
            100                 105                 110

Asn Lys Ala Leu Asp Phe Ile Ala Ser Lys Gly Val Lys Leu Val Ser
        115                 120                 125

Ile Gly Ala Glu Glu Ile Val Asp Gly Asn Ala Lys Met Thr Leu Gly
    130                 135                 140

Met Ile Trp Thr Ile Ile Leu Arg Phe Ala Ile Gln Asp Ile Ser Val
145                 150                 155                 160

Glu Glu Thr Ser Ala Lys Glu Gly Leu Leu Leu Trp Cys Gln Arg Lys
                165                 170                 175

Thr Ala Pro Tyr Lys Asn Val Asn Val Gln Asn Phe His Ile Ser Trp
            180                 185                 190

Lys Asp Gly Leu Ala Phe Asn Ala Leu Ile His Arg His Arg Pro Glu
        195                 200                 205

Leu Ile Glu Tyr Asp Lys Leu Arg Lys Asp Asp Pro Val Thr Asn Leu
    210                 215                 220

Asn Asn Ala Phe Glu Val Ala Glu Lys Tyr Leu Asp Ile Pro Lys Met
225                 230                 235                 240

Leu Asp Ala Glu Asp Ile Val Asn Thr Ala Arg Pro Asp Glu Lys Ala
                245                 250                 255

Ile Met Thr Tyr Val Ser Ser Phe Tyr His Ala Phe Ser Gly Ala Gln
            260                 265                 270

Lys Ala Glu Thr Ala Ala Asn Arg Ile Cys Lys Val Leu Ala Val Asn
        275                 280                 285

Gln Glu Asn Glu His Leu Met Glu Asp Tyr Glu Lys Leu Ala Ser Asp
    290                 295                 300

Leu Leu Glu Trp Ile Arg Arg Thr Ile Pro Trp Leu Glu Asp Arg Val
305                 310                 315                 320

Pro Gln Lys Thr Ile Gln Glu Met Gln Gln Lys Leu Glu Asp Phe Arg
                325                 330                 335

Asp Tyr Arg Arg Val His Lys Pro Pro Lys Val Gln Glu Lys Cys Gln
            340                 345                 350

Leu Glu Ile Asn Phe Asn Thr Leu Gln Thr Lys Leu Arg Leu Ser Asn
        355                 360                 365

Arg Pro Ala Phe Met Pro Ser Glu Gly Lys Met Val Ser Asp Ile Asn
    370                 375                 380

Asn Gly Trp Gln His Leu Glu Gln Ala Glu Lys Gly Tyr Glu Glu Trp
385                 390                 395                 400

Leu Leu Asn Glu Ile Arg Arg Leu Glu Arg Leu Asp His Leu Ala Glu
                405                 410                 415
```

Lys Phe Arg Gln Lys Ala Ser Ile His Glu Ala Trp Thr Asp Gly Lys
                420                 425                 430

Glu Ala Met Leu Lys His Arg Asp Tyr Glu Thr Ala Thr Leu Ser Asp
            435                 440                 445

Ile Lys Ala Leu Ile Arg Lys His Glu Ala Phe Glu Ser Asp Leu Ala
    450                 455                 460

Ala His Gln Asp Arg Val Glu Gln Ile Ala Ala Ile Ala Gln Glu Leu
465                 470                 475                 480

Asn Glu Leu Asp Tyr Tyr Asp Ser His Asn Val Asn Thr Arg Cys Gln
                485                 490                 495

Lys Ile Cys Asp Gln Trp Asp Ala Leu Gly Ser Leu Thr His Ser Arg
                500                 505                 510

Arg Glu Ala Leu Glu Lys Thr Glu Lys Gln Leu Glu Ala Ile Asp Gln
            515                 520                 525

Leu His Leu Glu Tyr Ala Lys Arg Ala Ala Pro Phe Asn Asn Trp Met
    530                 535                 540

Glu Ser Ala Met Glu Asp Leu Gln Asp Met Phe Ile Val His Thr Ile
545                 550                 555                 560

Glu Glu Ile Glu Gly Leu Ile Ser Ala His Asp Gln Phe Lys Ser Thr
                565                 570                 575

Leu Pro Asp Ala Asp Arg Glu Arg Glu Ala Ile Leu Ala Ile His Lys
                580                 585                 590

Glu Ala Gln Arg Ile Ala Glu Ser Asn His Ile Lys Leu Ser Gly Ser
            595                 600                 605

Asn Pro Tyr Thr Thr Val Thr Pro Gln Ile Ile Asn Ser Lys Trp Glu
    610                 615                 620

Lys Val Gln Gln Leu Val Pro Lys Arg Asp His Ala Leu Leu Glu Glu
625                 630                 635                 640

Gln Ser Lys Gln Gln Ser Asn Glu His Leu Arg Arg Gln Phe Ala Ser
                645                 650                 655

Gln Ala Asn Val Val Gly Pro Trp Ile Gln Thr Lys Met Glu Glu Ile
                660                 665                 670

Gly Arg Ile Ser Ile Glu Met Asn Gly Thr Leu Glu Asp Gln Leu Ser
            675                 680                 685

His Leu Lys Gln Tyr Glu Arg Ser Ile Val Asp Tyr Lys Pro Asn Leu
    690                 695                 700

Asp Leu Leu Glu Gln Gln His Gln Leu Ile Gln Glu Ala Leu Ile Phe
705                 710                 715                 720

Asp Asn Lys His Thr Asn Tyr Thr Met Glu His Ile Arg Val Gly Trp
                725                 730                 735

Glu Gln Leu Leu Thr Thr Ile Ala Arg Thr Ile Asn Glu Val Glu Asn
                740                 745                 750

Gln Ile Leu Thr Arg Asp Ala Lys Gly Ile Ser Gln Glu Gln Met Gln
            755                 760                 765

Glu Phe Arg Ala Ser Phe Asn His Phe Asp Lys Asp His Gly Gly Ala
    770                 775                 780

Leu Gly Pro Glu Glu Phe Lys Ala Cys Leu Ile Ser Leu Gly Tyr Asp
785                 790                 795                 800

Val Glu Asn Asp Arg Gln Gly Glu Ala Glu Phe Asn Arg Ile Met Ser
                805                 810                 815

Leu Val Asp Pro Asn His Ser Gly Leu Val Thr Phe Gln Ala Phe Ile
                820                 825                 830

-continued

```
Asp Phe Met Ser Arg Glu Thr Thr Asp Thr Asp Thr Ala Asp Gln Val
            835             840             845

Ile Ala Ser Phe Lys Val Leu Ala Gly Asp Lys Asn Phe Ile Thr Ala
    850             855             860

Glu Glu Leu Arg Arg Glu Leu Pro Pro Asp Gln Ala Glu Tyr Cys Ile
865             870             875                     880

Ala Arg Met Ala Pro Tyr Gln Gly Pro Asp Ala Val Pro Gly Ala Leu
                885             890             895

Asp Tyr Lys Ser Phe Ser Thr Ala Leu Tyr Gly Glu Ser Asp Leu
            900             905             910
```

MONOCLONAL ANTIBODIES AGAINST ALPHA-ACTININ-4 ANTIGENS, AND USES THEREFOR

This is a U.S. National Stage Entry of International Application No. PCT/US2011/67135, filed Dec. 23, 2011, which claims the benefit of U.S. Provisional Application No. 61/430,874, filed Jan. 7, 2011 and U.S. Provisional Application No. 61/428,159, filed Dec. 29, 2010, all of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Sep. 20, 2013, is named 12112.0006-00000_SL.txt and is 43,377 bytes in size.

BACKGROUND OF THE INVENTION

1. Field of the Invention

The present invention provides and includes monoclonal antibodies (MoAbs or mAbs) specific for ALPHA-ACTININ-4 antigens, hybridoma lines that secrete these ALPHA-ACTININ-4 mAbs or fragments thereof, and the use of such mAbs or fragments thereof to detect ALPHA-ACTININ-4 antigens, particularly those expressed by cancer cells. The present invention also includes chimeric and humanized antibodies based upon these mAbs, processes for producing monoclonal, chimeric, and humanized antibodies using recombinant DNA technology, and their therapeutic uses, particularly in the treatment of cancer.

2. Description of the Background Art

Antibodies (also referred to as immunoglobulins) are constructed from four polypeptide chains, two heavy chains and two light chains. The two heavy chains are linked to each other by disulfide bonds and each heavy chain is linked to a light chain by a disulfide bond. There are two types of light chain, lambda (γ) and kappa (κ). There are five main heavy chain classes (or isotypes) which determine the functional activity of an antibody molecule: IgM, IgD, IgG, IgA and IgE.

Each chain contains distinct sequence domains. The light chain includes two domains, a variable domain ($V_L$) and a constant domain ($C_L$). The heavy chain includes four domains, a variable domain ($V_H$) and three constant domains ($C_{H1}$, $C_{H2}$ and $C_{H3}$, collectively referred to as $C_H$). The variable regions of both light ($V_L$) and heavy ($V_H$) chains determine binding recognition and specificity to the antigen. The constant region domains of the light ($C_L$) and heavy ($C_H$) chains confer important biological properties such as antibody chain association, secretion, transplacental mobility, complement binding, and binding to Fc receptors.

The variable domain is responsible for antigen-specific binding, and the constant domains carry out effector functions. The variable domain is divided into complementarity determining regions (CDR1, CDR2 and CDR3) and framework regions (FWR1, FWR2, and FWR3). Using the Kabat residue numbering system, CDRs 1, 2, and 3 are delineated by amino acid positions 31-35, 50-65, and 95-102 for heavy chains, and amino acid positions 24-34, 50-56, and 89-97 for light chains. While these amino acid positions define the boundaries of each CDR, the lengths of the CDRs can vary. The CDRs create the antigen binding pocket of the molecule through the interaction between heavy and light chain variable regions while the framework regions provide the scaffolding on which the antigen binding pocket sits. Occasionally, residues from nonhypervariable or framework regions (FWRs) influence the overall domain structure and hence the combining site.

There are two major methods for generating vertebrate antibodies: generation of polyclonal antibodies in situ by mammalian B lymphocytes and generation of monoclonal antibodies in cell culture by B cell hybrids. To generate antibodies in situ, an animal (such as a mouse or rabbit) is injected with an antigen. Several weeks later, blood is drawn from the animal and centrifuged. The resulting serum contains antibodies against the injected antigen. The resulting antibodies are polyclonal antibodies because they are products of many different populations of antibody producing cells and hence differ somewhat in their precise specificity and affinity for the antigen.

Monoclonal antibodies are produced using hybridoma technology in which an antibody producing cell is fused with a tumor cell that has the capacity for unlimited proliferation. In contrast to polyclonal antibodies, monoclonal antibodies are homogeneous because they are synthesized by a population of identical cells that are derived from a single hybridoma cell.

However, the use of monoclonal antibodies in humans is severely restricted when the monoclonal antibody is produced in a non-human animal. Repeated injections in humans of a "foreign" antibody, such as a mouse antibody, may lead to harmful hypersensitivity reactions, i.e., anti-mouse antibody (HAMA) or an anti-idiotypic, response. The HAMA response makes repeated administrations ineffective due to an increased rate of clearance from the patient's serum and/or allergic reactions by the patient.

Attempts have been made to manufacture human-derived monoclonal antibodies using human hybridomas. Unfortunately, yields of monoclonal antibodies from human hybridoma cell lines are relatively low compared to mouse hybridomas. Additionally, human cell lines expressing immunoglobulins are relatively unstable compared to mouse cell lines, and the antibody producing capability of these human cell lines is transient. Thus, while human immunoglobulins are highly desirable, human hybridoma techniques have not yet reached the stage where human monoclonal antibodies with the required antigenic specificities can be easily obtained.

Thus, antibodies of non-human origin are typically genetically engineered to create chimeric or humanized antibodies. Such genetic engineering results in antibodies with a reduced risk of a HAMA response compared to that expected after injecting a human patient with a mouse antibody. For example, chimeric antibodies can be formed by grafting non-human variable regions to human constant regions. Humanized antibodies are formed by grafting non-human complementarity determining regions (CDRs) onto human framework regions (FWRs). Typically, humanized monoclonal antibodies are formed by grafting all six (three light chain and three heavy chain) CDRs from a non-human antibody into FWRs of a human antibody. However, these modified antibodies still retain various non-human light and heavy chain variable regions: the chimeric antibodies retain entire non-human variable regions, and CDR-grafted antibodies retain CDR of non-human origin. Such non-human regions can elicit an immunogenic reaction when administered to a human patient. Thus, many humanized mAbs remain immunogenic.

It has been shown that not all residues of CDRs are critical in the complementarity of antigen/antibody surfaces. Known structures of the antigen-antibody complexes suggest that only 20-33% of CDR residues are involved in antigen contact.

A comprehensive analysis of the available data of the sequences and the three dimensional structure of antibody combining sites can be used to identify CDR residues that may be critical in the antigen antibody interaction. These residues are designated as specificity determining residues (SDRs), and they may be shared among antibodies to a particular antigen.

During the process of oncogenesis, a number of cell-surface molecules or markers appear on cells. Such tumor-related markers may include, but are not limited to, oncofetoproteins, neoglycoproteins, sphignolipids, and modifications of existing surface proteins. Such new or altered structures are often shed from the tumor cell surface and appear in the serum or in other biological fluids. The detection of any of these substances or "tumor markers" or "biomarkers" serves as the basis for diagnosing or monitoring the progress of neoplastic disease.

Using monoclonal antibody (mAb or MoAb) technology, it has become possible to obtain pure antibody populations which permit better purification and characterization of the various tumor markers and tumor-associated antigens that are useful for immunodiagnosis or immunotherapy. Many mAbs have been described that have varying degrees of selectivity for tumor antigens (versus normal cell surface markers); some of these tumor antigens are broadly represented across several or many tumor types, whereas others appear to be truly tumor or cancer cell-specific.

ALPHA-ACTININ-4 may be a useful marker for the detection of neuroendocrine pulmonary tumors (NEPT) (see N. H. Cho et al., J. Proteome Res. 5(3):643-50 (2006)), and for the detection of hepatocarcinoma (HCC) metastasis (see Z. Dai et al., Proteomics 6(21):5857-67 (2006)).

Accordingly, there is a need for an antibody molecule to selectively detect diseases, such as solid tumors, characterized by the expression or localization of ALPHA-ACTININ-4 gene products that can be used repeatedly and produced easily and efficiently. There is also a need for an antibody molecule which has high affinity for gene products of ALPHA-ACTININ-4 and homologues thereof.

SUMMARY OF THE INVENTION

The present invention includes monoclonal antibodies and fragments thereof specific for expression products of ALPHA-ACTININ-4, and the expression products of variants and homologues of ALPHA-ACTININ-4, which are useful in methods and kits for detecting solid tumors that express ALPHA-ACTININ-4, and in methods and compositions for treating solid tumors that express ALPHA-ACTININ-4. The present invention is also directed towards methods of making the mAbs, and methods of using the mAbs. The invention is further directed towards methods of targeting ALPHA-ACTININ-4 expression products using the mAbs of the present invention, as well as inhibiting peptides, siRNA, antisense oligonucleotides, vaccines, and chemical compounds developed using ALPHA-ACTININ-4 expression products discovered in accordance with the present invention as drug development targets. The present invention also provides an antibody capable of preferentially binding to a soluble form of an ALPHA-ACTININ-4.

In a first aspect, the present invention provides an antibody specific for an ALPHA-ACTININ-4 antigen, including the heavy chain CDR antigen binding site amino acid sequences CDR1, CDR2, and CDR3 as set forth in FIG. 4, and the light chain CDR antigen binding site amino acid sequences CDR1, CDR2, and CDR3 as set forth in FIG. 5. The present invention also provides an antibody specific for an ALPHA-ACTININ-4 antigen, comprising one or more of the heavy chain CDR antigen binding site amino acid sequences set forth in FIG. 4, and one or more of the light chain CDR antigen binding site amino acid sequences set forth in FIG. 5.

These antibodies are specific for ALPHA-ACTININ-4, and may be used to detect a soluble form of the ALPHA-ACTININ-4 protein. The soluble protein has a molecular weight of about 35-40 kDa, as measured by gradient polyacrylamide gel electrophoresis.

The antibodies may optionally be immobilized on a solid phase, detectably labeled, or conjugated to a cytotoxic radionuclide, a cytotoxic drug, or a cytotoxic protein.

Another aspect of the invention provides compositions comprising any of these antibodies, optionally in combination with a pharmaceutically acceptable carrier.

In another aspect, the present invention provides an isolated DNA sequence which encodes the heavy chain of an antibody molecule, wherein said antibody molecule has specificity for ALPHA-ACTININ-4 antigens and wherein the variable domain of said heavy chain comprises a CDR having the antigen binding site amino acid sequences CDR1, CDR2, and CDR3 set forth in FIG. 6.

In yet another aspect, the present invention provides an isolated DNA sequence which encodes the light chain of an antibody molecule, wherein said antibody molecule has specificity for ALPHA-ACTININ-4 antigens and further wherein the variable domain of said light chain comprises a CDR having the antigen binding site amino acid sequences CDR1, CDR2, and CDR3 set forth in FIG. 7.

The isolated DNA sequences may be incorporated into a cloning or expression vector, which may in turn be used to transform a host cell. The transformed host cells may be used in a process for the production of an antibody molecule having specificity for ALPHA-ACTININ-4 antigens, including culturing the host cells and isolating the antibody molecules they produce.

In a further aspect, the present invention also provides an immunoassay for detecting an ALPHA-ACTININ-4 antigen which binds to a monoclonal antibody having the one or more of the heavy chain CDR antigen binding site sequences set forth in FIG. 6, and one or more of the light chain CDR antigen binding site sequences set forth in FIG. 7, comprising: (a) contacting said sample with an effective binding amount of an antibody specific for an ALPHA-ACTININ-4 antigen, comprising the heavy chain CDR antigen binding site sequences CDR1, CDR2, and CDR3, selected from the group consisting of SEQ ID NOs: 2-4, and the light chain CDR antigen binding site sequences CDR1, CDR2, and CDR3, selected from the group consisting of SEQ ID NOs: 7-9; and (b) detecting said antigen by detecting the binding of the antibody to an ALPHA-ACTININ-4 antigen. The present invention also provides an immunoassay for detecting an ALPHA-ACTININ-4 antigen which binds to a monoclonal antibody having the one or more of the heavy chain CDR antigen binding site amino acid sequences set forth in FIG. 6, and one or more of the light chain CDR antigen binding site amino acid sequences set forth in FIG. 7, comprising: (a) contacting said sample with an effective binding amount of one of the antibodies of the invention; and (b) detecting said antigen by detecting the binding of the antibody to the ALPHA-ACTININ-4 antigen. This immunoassay may be used to detect cancer cells expressing a ALPHA-ACTININ-4 antigen, particularly cancer cells selected from the group consisting of breast, ovary, head/neck, and brain cancers. In another aspect the immunoassay may be used to detect cancer cells expressing a ALPHA-ACTININ-4 antigen, particularly breast cancer cells.

In another aspect, the present invention provides a kit for the immunohistochemical detection of carcinoma comprising: (a) a monoclonal antibody having one or more of the heavy chain CDR antigen binding site amino acid sequences set forth in FIG. 6, and one or more of the light chain CDR antigen binding site amino acid sequences set forth in FIG. 7; and (b) a secondary antibody conjugated to a detectable label.

In a still further aspect, the present invention provides a method for diagnosing cancer in humans comprising: (a) removing a specimen from a patient suspected of having a cancer; (b) contacting the specimen with a monoclonal antibody having one or more of the heavy chain CDR antigen binding site amino acid sequences set forth in FIG. 6, and one or more of the light chain CDR antigen binding site amino acid sequences set forth in FIG. 7; (c) labeling the specimen; and (d) detecting the presence of the antigen-antibody complex by the label. The method of diagnosing cancer may be performed in vivo or in vitro, and the cancer being diagnosed may be selected from the group consisting of solid tumors of the breast, ovary, head/neck, and brain. In another aspect, the method of diagnosing cancer may be performed in vivo or in vitro, and the cancer being diagnosed may be a solid breast cancer tumor.

In an additional aspect, the present invention provides a method for developing drugs useful in treating and/or diagnosing diseases characterized by the expression of gene products of ALPHA-ACTININ-4 and homologues thereof, including identifying gene products expressed by ALPHA-ACTININ-4 and homologues thereof, in a subject having a disease, and utilizing said gene products as biomarkers in the development and identification of drugs 195 selected from the group consisting of ALPHA-ACTININ-4 mAbs, inhibiting peptides, siRNA, antisense oligonucleotides, vaccines, and chemical compounds, which specifically target said gene products.

BRIEF DESCRIPTION OF THE DRAWINGS

FIG. 1. Mascot Search Results of protein isolated with Alper ALPHA-ACTININ-4 mAb. FIG. 1 also discloses SEQ ID NOs: 30-52 respectfully, in order of appearance from top to bottom.

FIG. 4. Framework and complementary determining regions designated for Alper-ALPHA-ACTININ-4 mAb heavy chain (SEQ ID NO:1). The bold residues set forth in underlined text indicate the specificity determining residues (SDRs).

FIG. 5. Framework and complementary determining regions designated for Alper-ALPHA-ACTININ-4 mAb light chain (SEQ ID NO:5). The bold residues set forth in underlined text indicate the specificity determining residues (SDRs).

Figure 6C:
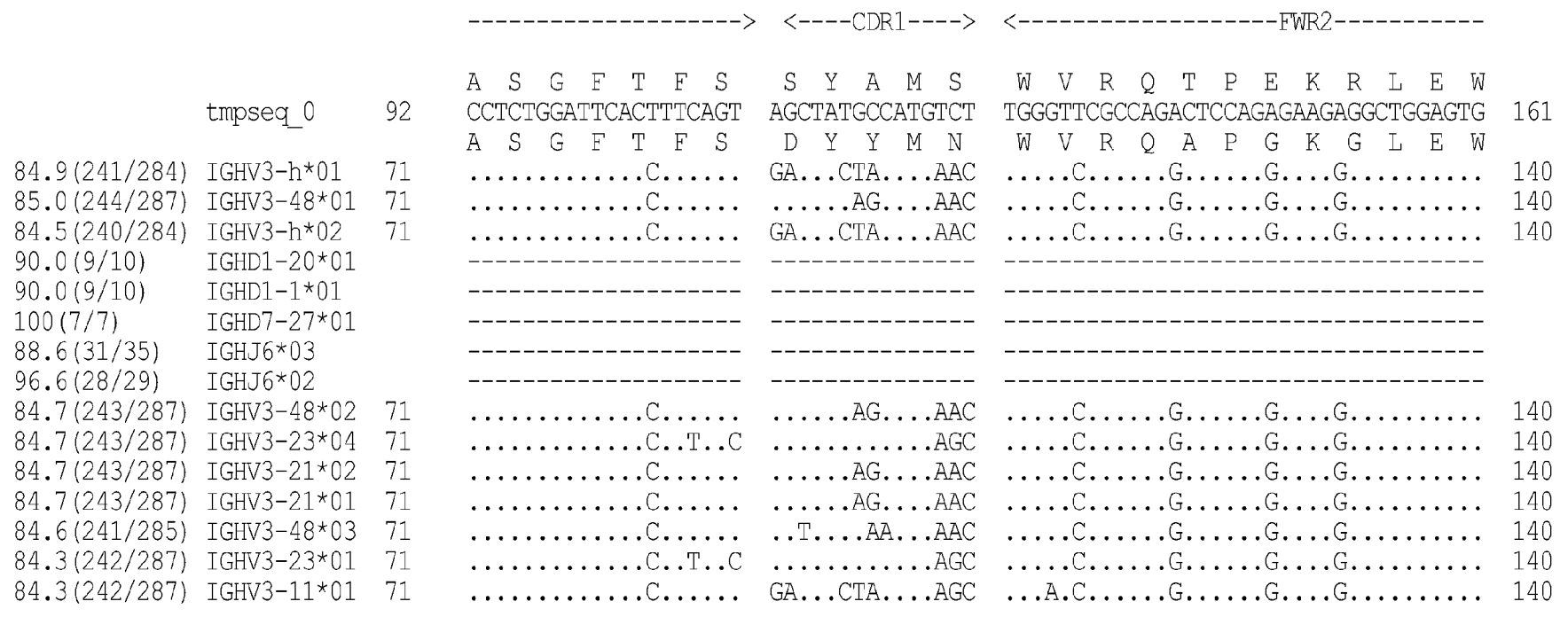
Figure 6D:
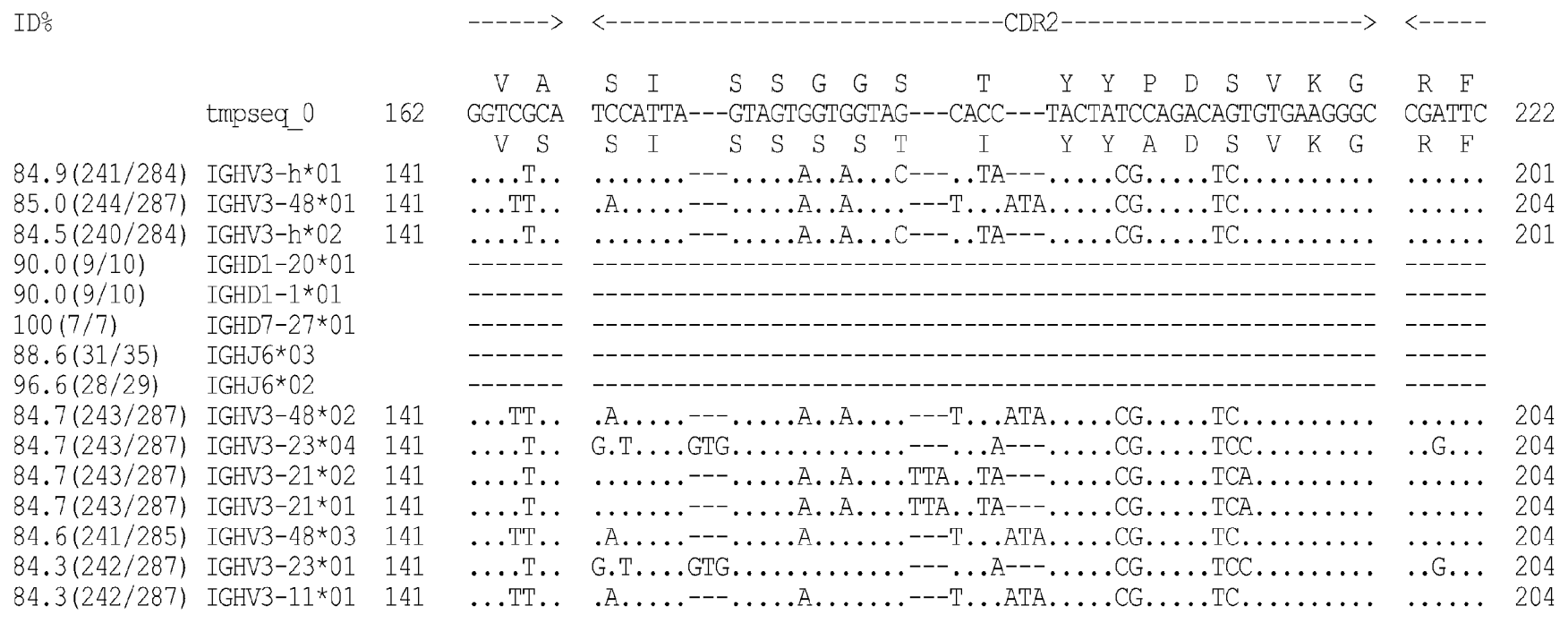
Figure 6E:
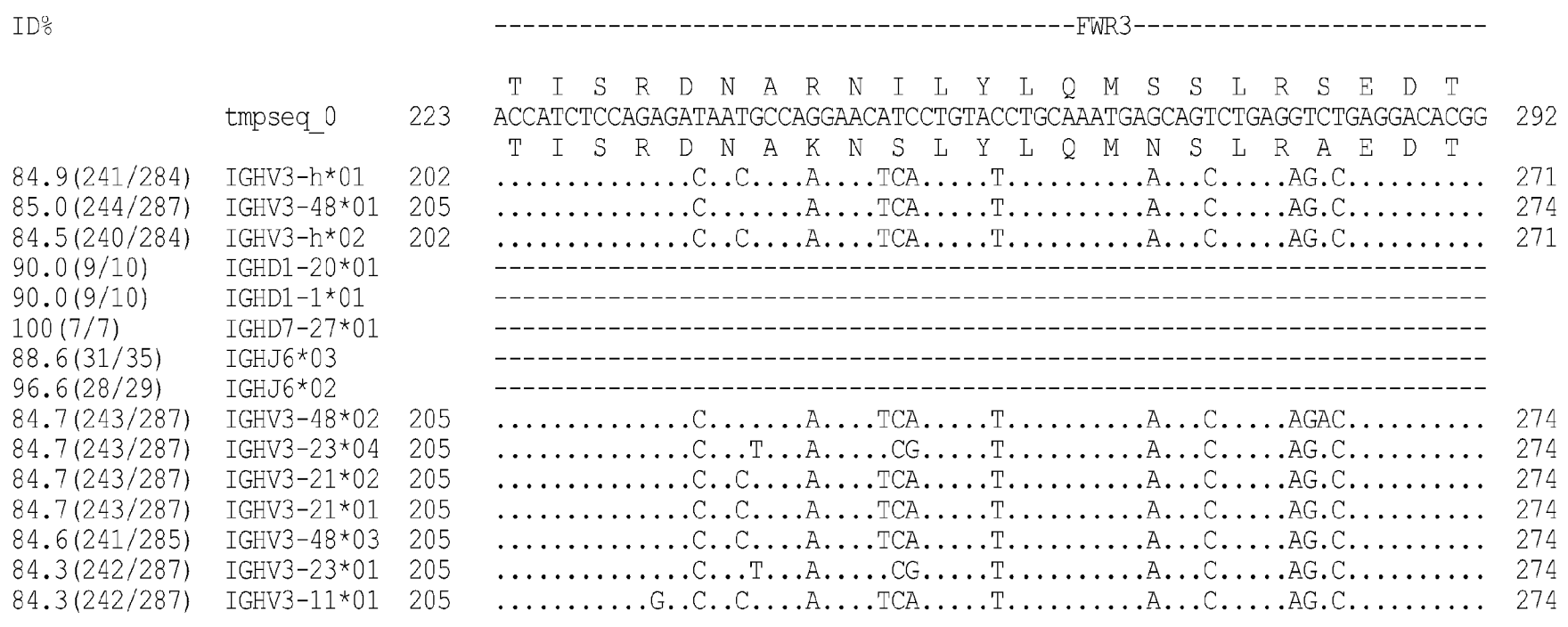

FIG. 6. Alper-ALPHA-ACTININ-4 mAb heavy chain sequence information. FWRs and CDRs of the heavy chain of Alper-ALPHA-ACTININ-4 mAb heavy chain, in which the polypeptide sequence provided in the top line (SEQ ID NO:1) corresponds to the sequence of the Alper-ALPHA-ACTININ-4 mAb. Amino acid residues are numbered using the convention of Kabat et al., (1991) Sequences of Proteins of Immunological Interest, 5th Edition, Department of Health and Human Services, Public Health Service, National Institutes of Health, Bethesda (NIH Publication No. 91-3242). The next line from top is the nucleotide sequence of Alper-ALPHA-ACTININ-4 mAb heavy chain (SEQ ID NO: 9). The next line down is an antibody heavy chain amino acid sequence (SEQ ID NO: 54). FIG. 6 also discloses SEQ ID NOs: 53 and 55-67 respectfully, in order of next appearance from top to bottom.

Figure 7B:
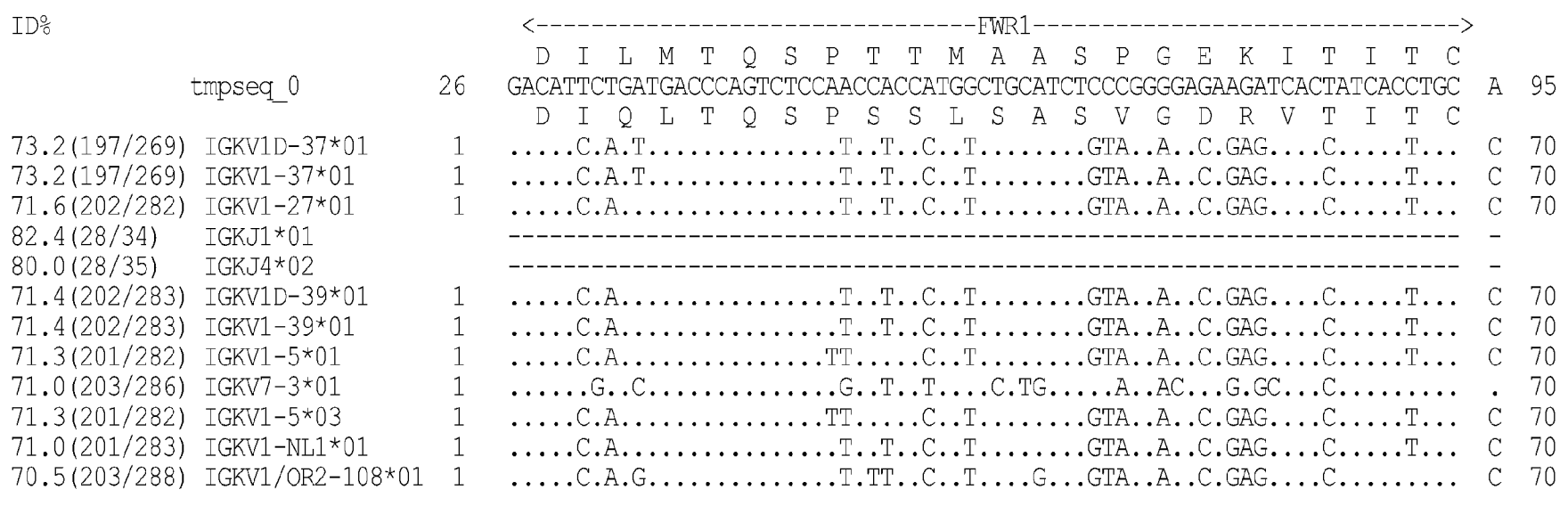
Figure 7D:
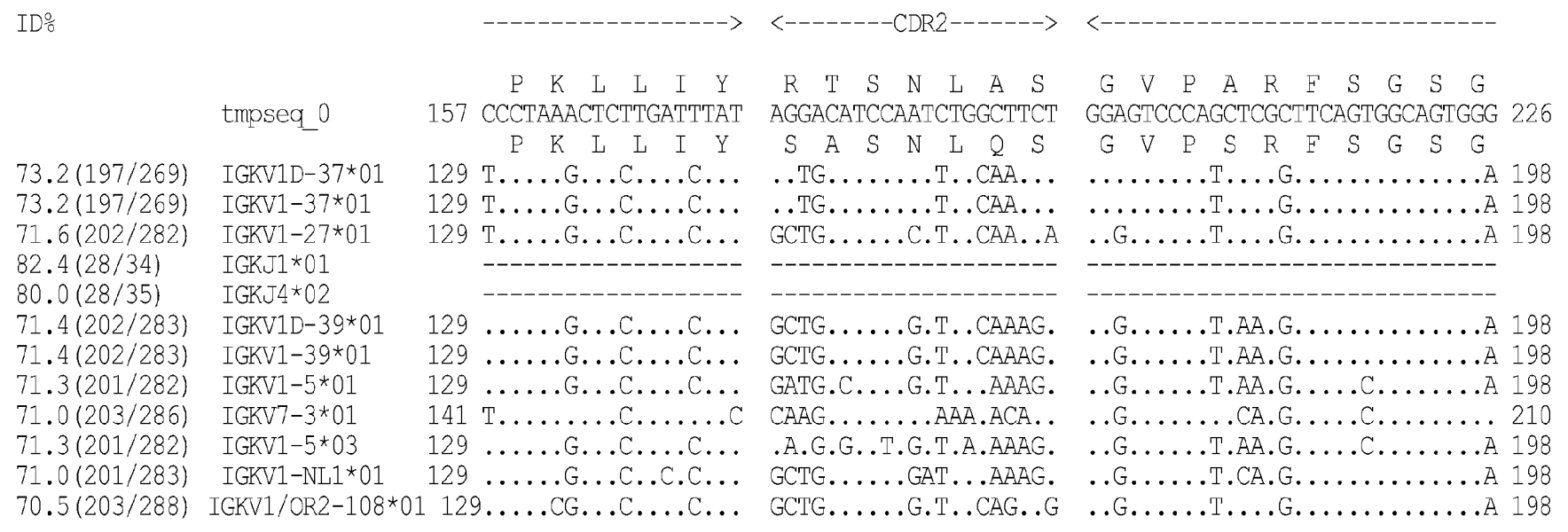

FIG. 7. Alper-ALPHA-ACTININ-4 mAb light chain sequence information. FWRs and CDRs of the light chain of Alper-ALPHA-ACTININ-4 mAb light chain, in which the polypeptide sequence provided in the top line (SEQ ID NO: 5) corresponds to the sequence of the Alper-ALPHA-ACTININ-4 mAb light chain. Amino acid residues are numbered using the convention of Kabat et al. The next line from top is the nucleotide sequence of Alper-ALPHA-ACTININ-4 mAb light chain (SEQ ID NO: 10). The next line down is an antibody light chain amino acid sequence (SEQ ID NO: 69). FIG. 7 also discloses SEQ ID NOs: 68 and 70-80 respectfully, nucleic acid sequences in order of next appearance from top to bottom.

BRIEF DESCRIPTION OF CERTAIN SEQUENCES

Figure 2:
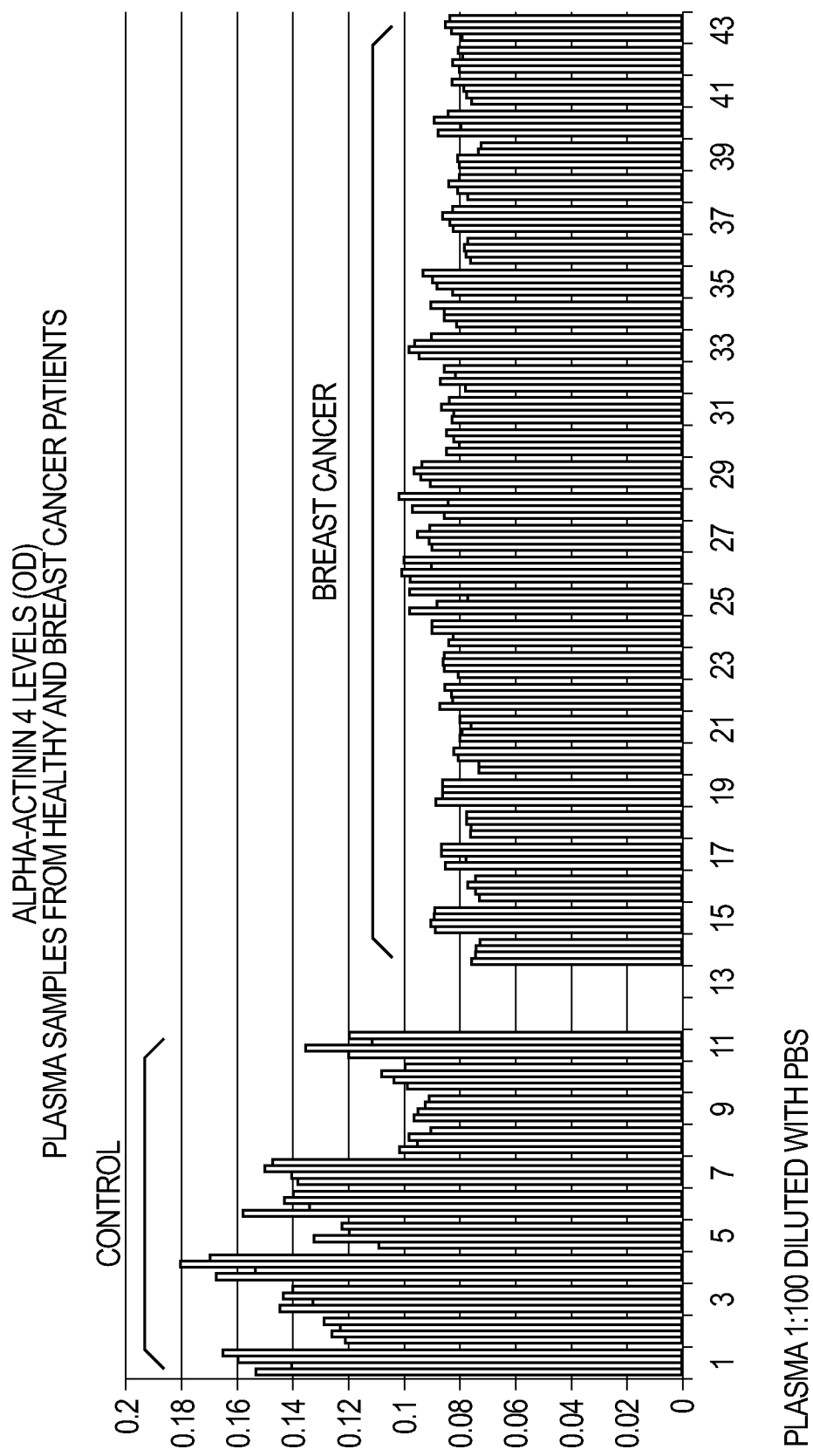
FIG. 2. Breast Cancer Disease Patient Plasma and Control Healthy Plasma ALPHA-ACTININ-4 Levels.

SEQ ID NO: 1 shows the amino acid sequence of an Alper-ALPHA-ACTININ-4 mAb Heavy Chain.

SEQ ID NO: 2 shows CDR1 of an Alper-ALPHA-ACTININ-4 mAb Heavy Chain.

SEQ ID NO: 3 shows CDR2 of an Alper-ALPHA-ACTININ-4 mAb Heavy Chain.

SEQ ID NO: 4 shows CDR3 of an Alper-ALPHA-ACTININ-4 mAb Heavy Chain.

SEQ ID NO: 5 shows the amino acid sequence of Alper-ALPHA-ACTININ-4 mAb Kappa Chain.

SEQ ID NO: 6 shows CDR1 of an Alper-ALPHA-ACTININ-4 mAb Kappa Chain.

SEQ ID NO: 7 shows CDR2 of an Alper-ALPHA-ACTININ-4 mAb Kappa Chain.

SEQ ID NO: 8 shows CDR3 of an Alper-ALPHA-ACTININ-4 mAb Kappa Chain.

SEQ ID NO: 9 shows the nucleic acid sequence of an Alper-ALPHA-ACTININ-4 mAb Heavy Chain.

SEQ ID NO: 10 shows the nucleic acid sequence of an Alper-ALPHA-ACTININ-4 mAb Kappa Chain.

SEQ ID NOs: 11-29 show the amino acid sequence of potential Alper-ALPHA-ACTININ-4 epitopes.

SEQ ID NOs: 30-52 show the Mascot Search Results of protein isolated with Alper ALPHA-ACTININ-4 mAb.

SEQ ID NOs: 53 and 55-67 show antibody sequences.

SEQ ID NO: 54 shows an antibody amino acid sequences.

SEQ ID NOs: 68 and 70-80 show antibody nucleotide sequences.

SEQ ID NO: 69 shows an antibody amino acid sequence.

SEQ ID NO: 81 shows the sequence of ALPHA-ACTININ-4 antigen.

DETAILED DESCRIPTION

The present invention includes monoclonal antibodies (MoAbs or mAbs) or fragments thereof specific for ALPHA-ACTININ-4 antigens, hybridoma lines that secrete these ALPHA-ACTININ-4 mAbs of fragments thereof, and the use of such mAbs to detect ALPHA-ACTININ-4 antigens, particularly those expressed by cancer cells. The present invention also includes chimeric and humanized antibodies based upon these new mAbs, processes for producing monoclonal, chimeric, and humanized antibodies using recombinant DNA technology, and their therapeutic uses, particularly in the treatment of cancer. The present invention further provides methods and kits, for use in research and diagnostic applications, for the immunodetection and immunotherapy of solid tumors which express ALPHA-ACTININ-4 antigens, particularly solid tumors of the breast, ovary, head/neck, and brain, as well as methods and kits for the detection and purification of carcinoma-associated ALPHA-ACTININ-4 antigens. In addition, the present invention provides and includes the discovery of ALPHA-ACTININ-4 and homologues thereof, and gene products expressed by ALPHA-ACTININ-4 and its homologues, which may be utilized as biomarkers and targeted by ALPHA-ACTININ-4 mAbs, inhibiting peptides, siRNA, antisense oligonucleotides, vaccines, and chemical compounds. In another aspect, the present invention further provides methods and kits, for use in research and diagnostic applications, for the immunodetection and immunotherapy of solid tumors which express ALPHA-ACTININ-4 antigens, particularly solid tumors of the breast.

1. Definitions

Antibody: This refers to single chain, two-chain, and multi-chain proteins and glycoproteins belonging to the classes of polyclonal, monoclonal, chimeric and hetero immunoglobulins (monoclonal antibodies being preferred); it also includes synthetic and genetically engineered variants of these immunoglobulins. "Antibody fragment" includes Fab, Fab', F(ab')$_2$, and Fv fragments, as well as any portion of an antibody having specificity toward a desired target epitope or epitopes.

Monoclonal Antibody: This refers to antibodies that are identical because they are produced by one type of immune cell that are all clones of a single parent cell. The monoclonal antibodies of the present invention may include intact monoclonal antibodies, antibody fragments, conjugates, or fusion proteins, which contain a $V_H$-$V_L$ pair where the CDRs form the antigen binding site.

Chimeric Antibody: This refers to an antibody which includes sequences derived from two different antibodies, which typically are of different species. Most typically, chimeric antibodies include human and non-human antibody fragments, generally human constant and non-human variable regions.

Humanized Antibody: This refers to an antibody derived from a non-human antibody, and a human antibody which retains or substantially retains the antigen-binding properties of the parent antibody but which is less immunogenic in humans.

Antibody Conjugates, Fusion Proteins, and Bispecific Antibodies: This refers to monoclonal antibodies conjugated by chemical methods with radionuclides, drugs, macromolecules, or other agents.

Antigen: This refers to a molecule or a portion of a molecule capable of being bound by an antibody which is additionally capable of inducing an animal to produce an antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

Epitope: This refers to that portion of any molecule capable of being recognized by, and bound by, an antibody. In general, epitopes consist of chemically active surface groupings of molecules, for example, amino acids or sugar side chains, and have specific three-dimensional structural characteristics as well as specific charge characteristics. The epitopes of interest for the present invention are epitopes comprising amino acids.

Complementarity Determining Region, or CDR: This refers to amino acid sequences which together define the binding affinity and specificity of the natural Fv region of a native immunoglobulin binding site. The light and heavy chains of an immunoglobulin each have three CDRs. By definition, the CDRs of the light chain are bounded by the residues at positions corresponding to 24 and 35 (CDR1), 51 and 57 (CDR2), 90 and 98 (CDR3) of SEQ ID NO:5; the CDRs of the heavy chain are bounded by the residues at positions corresponding to 28 and 32 (CDR1), 47 and 62 (CDR2), and 93 and 104 (CDR3) of SEQ ID NO:1, using the numbering convention delineated by Kabat et al., (1991) Sequences of Proteins of Immunological Interest, 5th Edition, Department of Health and Human Services, Public Health Service, National Institutes of Health, Bethesda (NIH Publication No. 91-3242).

Framework Region or FWR: This refers to amino acid sequences interposed between CDRs. These portions of the antibody serve to hold the CDRs in an appropriate orientation for antigen binding.

Specificity Determining Residue, or SDR: This refers to amino acid residues of an immunoglobulin that are directly involved in antigen contact.

Constant Region: This refers to the portion of the antibody molecule which confers effector functions. The heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. The light chain constant region can be of the kappa or lambda type, preferably the kappa type.

Immunogenicity: A measure of the ability of a targeting protein or therapeutic moiety to elicit an immune response (humoral or cellular) when administered to a recipient. The present invention is concerned with the immunogenicity of antibodies to ALPHA-ACTININ-4.

Immunoreactivity: A measure of the ability of an immunoglobulin to recognize and bind to a specific antigen.

ALPHA-ACTININ-4 Antibodies or ALPHA-ACTININ-4 mAbs: This refers to antibodies specific to expression products of the ALPHA-ACTININ-4 gene and homologues of the ALPHA-ACTININ-4 gene, which may include antibodies specific to modified forms of the expression product that are produced by cancer cells. The antibodies include variants, such as chimeric, humanized, and other variants known to those skilled in the art. ALPHA-ACTININ-4 antibodies are said to be specific for an ALPHA-ACTININ-4 antigen if they exhibit preferential binding to the same ALPHA-ACTININ-4 antigen as the Alper-ALPHA-ACTININ-4 at least 85% of the time, at least 90% of the time, or, in a preferred aspect, at least 95% of the time. An example of such an antibody is the Alper-ALPHA-ACTININ-4 mouse IgG2 monoclonal antibody.

ALPHA-ACTININ-4 Antigens: This refers to expression products generated by ALPHA-ACTININ-4, which may be used as antigens, target molecules, and/or biomarkers. The ALPHA-ACTININ-4 antigens may be produced by the ALPHA-ACTININ-4 gene and homologues of the ALPHA-ACTININ-4 gene, and may include various modifications introduced by the cells expressing the ALPHA-ACTININ-4 antigens, such as cancer cells. These ALPHA-ACTININ-4 antigens are useful for producing antibodies, siRNA, antisense oligomers, vaccines, and chemical compounds that target the expression of ALPHA-ACTININ-4.

Substantially Similar Binding Properties: This refers to a chimeric or humanized antibody or antibody fragment which retains the ability to specifically bind the antigen recognized by the parent antibody used to produce the chimeric antibody, humanized antibody, or antibody fragment. Preferably, the affinity of the chimeric antibody, humanized antibody, or antibody fragment is at least about 10% of the affinity of the parent antibody, more preferably at least about 25%, even more preferably at least about 50%. Most preferably, the chimeric antibody, humanized antibody, or antibody fragment exhibits antigen-binding affinity that is at least about 75% of the affinity of the parent antibody for an ALPHA-ACTININ-4 antigen. Methods for assaying antigen-binding affinity are well known in the art and include half-maximal binding assays, competition assays, and Scatchard analysis. In a preferred aspect, antigen-binding affinity is assayed using a competition assay. Such a comparison can be relative to Alper-ALPHA-ACTININ-4 mouse monoclonal antibody.

Substantially Homologous: Refers to immunoglobulin sequences that exhibit at least about 85% identity, more preferably about 90% identity, most preferably about 95% identity with a reference immunoglobulin, wherein % identity is determined by comparing the number identical of amino acid residues between the two immunoglobulins, wherein the positions of the amino acid residues are indicated using the Kabat numbering scheme.

Sameness for Monoclonal Antibody Products: For the purpose of determining sameness of monoclonal antibodies, and products thereof, the complementarity determining regions of the heavy and light chain variable regions are the principal molecular structural feature of a monoclonal antibody product. Two monoclonal antibodies may be considered the same if the amino acid sequences of the CDRs were the same, or if there were only minor amino acid differences between them. Whether differences in the amino acid sequences are minor may be determined by factors that include (but are not limited to) whether any particular residues have been established to be important for antigen binding. Amino acid differences outside the CDRs, or differences due to glycosylation patterns or post translational modifications do not result in different monoclonal antibodies. Changes in antibody structure that do not constitute differences between two monoclonal antibody products with the same CDRs include changes in the FWRs (i.e., humanizing a non-human derived monoclonal antibody or engineering certain framework residues that are important for antigen contact or for stabilizing the binding site, or changes in the constant region (i.e., changing the class or subclass of the constant region, changing specific amino acid residues which might alter an effector function, or changing the species from which the constant region is derived).

2. Antibodies Specific for ALPHA-ACTININ-4 Antigens

The ALPHA-ACTININ-4 mAbs of the present invention were developed using the human breast cancer cell line SKBR3 (available from the American Type Culture Collection as ATCC No. HTB30).

The mAbs of the present invention or fragments thereof target expression of ALPHA-ACTININ-4 antigen by cells, preferably human cells, more preferably human cancer cells, and most preferably human breast, ovarian, head/neck, and brain cancer cells. In another aspect, the mAbs of the present invention or fragments thereof target expression of ALPHA-ACTININ-4 antigen by human breast cancer cells. The ALPHA-ACTININ-4 antigens being expressed may include any form of the gene product, although particularly preferred embodiments relate to the detection of the soluble or secreted form of ALPHA-ACTININ-4. Also envisioned within the scope of the present invention are homologues of the ALPHA-ACTININ-4 gene that express modified proteins, modified ALPHA-ACTININ-4 antigens expressed by cancer cells, and mAbs that target such variants of ALPHA-ACTININ-4. The ALPHA-ACTININ-4 antigens included within the scope of the present invention may be derived from the known ALPHA-ACTININ-4 protein products, or to yet unknown variants thereof that are produced by cancer cells, such as variants with transcriptional modifications.

The present invention includes an ALPHA-ACTININ-4 mAbs and fragments thereof having antigen binding sites CDR1, CDR2, and CDR3, in both heavy and light chains, as described in FIGS. 4 and 5. The invention also relates to mAbs specific to ALPHA-ACTININ-4 expression products that contain antigen binding sites that are substantially homologous to these, or that result in substantially similar binding properties. The present invention also relates to new hybridoma lines, and the monoclonal antibody molecules (mAbs) that they secrete, which are specific to ALPHA-ACTININ-4 antigen expressed by cancer cells. The present invention also relates to chimeric and humanized antibodies based upon these mAbs. In an aspect, a ALPHA-ACTININ-4 mAb or fragment thereof of the present invention includes an antibody with full length variable regions of Alper-ALPHA-ACTININ-4.

The present invention includes processes for producing monoclonal, chimeric, and humanized antibodies using recombinant DNA technology, and to their therapeutic uses, particularly in the detection and/or treatment of cancer, particularly breast cancer, ovarian cancer, head/neck cancer, and brain cancer. However, the methods of the present invention are not limited to the detection and/or treatment of these cancers, and may be useful in the detection and/or treatment of any type of disease state that results in expression of ALPHA-ACTININ-4.

In addition to the specific amino acid sequences of the antigen binding sites of the heavy and light chains set forth in FIGS. 4 and 5, the present invention also encompasses mAbs that are specific to ALPHA-ACTININ-4 but which have FWR and/or CDR antigen binding site amino acid sequences that are not identical to those set forth in FIGS. 4 and 5. Such mAbs are included within the scope of the present invention if they are specific for the ALPHA-ACTININ-4 antigen, preferably at least 85% as specific, more preferably at least 90% as specific, and most preferably at least 95% as specific for the ALPHA-ACTININ-4 antigen as the mAbs of the present invention. According to one presently preferred embodiment, these variants of the mAbs of the present invention are as specific for the ALPHA-ACTININ-4 antigen as the mAbs of the present invention, or are more specific.

More particularly, mAbs that are specific to ALPHA-ACTININ-4 but which have FWR and/or CDR antigen binding site amino acid sequences that are not identical to those set forth in FIGS. 4 and 5 may possess the same specificity determining regions (SDRs) as the FWRs and/or CDRs of FIGS. 4 and 5 (set forth in bold, underlined text in these figures).

Modifications to the amino acid sequences of the antigen binding sites CDR1, CDR2, and CDR3 set forth in FIG. 4 (heavy chain) and FIG. 5 (light chain) may be found in either or both of the FWR and CDR sequences. Particularly envisioned are variations in the amino acid sequences in the third hypervariable regions on both the heavy and light chains, which have been found to be more diverse than the first two hypervariable regions, where the third hypervariable region on the heavy chain is more diverse than that on the light chain. According to certain aspects of the invention, the variations result in antibodies having substantially homologous amino acid sequences, and/or in antibodies having substantially similar binding properties Humanized variants of the antibodies or antibody fragments of the invention may contain a reduced murine content, and consequently, reduced immunogenicity, when compared to the murine ALPHA-ACTININ-4 mAbs of the present invention. Nonetheless, the variants included within the scope of the invention retain a binding affinity that is substantially similar to that of the ALPHA-ACTININ-4 mAbs of the present invention. A first aspect of the invention provides CDR variants of humanized ALPHA-ACTININ-4 mAbs in which 1, 2, 3, 4, 5, or 6 (three or fewer heavy chain and three or fewer light chain) CDRs are present. Less than all six CDRs may be present. A second aspect of the invention provides SDR variants of humanized ALPHA-ACTININ-4 mAbs in which only Specificity Determining Regions (SDRs) of at least one CDR from the ALPHA-ACTININ-4 mAbs are present in the humanized antibodies. The SDRs are selected from Table 1 or Table 2.

TABLE 1

Specificity-Determining Residues in Alper-ALPHA-ACTININ-4 mAb Heavy Chain (SEQ ID NO. 1).

| Position | Residue |
|---|---|
| 2 | E |
| 16 | K |
| 28 | S |
| 30 | A |
| 32 | S |
| 37 | T |
| 39 | E |
| 41 | R |
| 46 | A |
| 51 | G |
| 52 | G |
| 53 | S |
| 54 | T |
| 57 | P |
| 72 | R |
| 74 | I |
| 80 | S |
| 84 | S |
| 89 | M |

TABLE 2

Specificity-Determining Residues in Alper-ALPHA-ACTININ-4 mAb Light Chain (SEQ ID NO. 5).

| Position | Residue |
|---|---|
| 3 | L |
| 4 | M |
| 9 | T |
| 10 | T |
| 11 | M |
| 12 | A |
| 15 | P |
| 17 | E |
| 18 | K |
| 19 | I |
| 24 | S |
| 25 | A |
| 27 | S |
| 28 | S |
| 31 | S |
| 32 | N |
| 35 | H |
| 38 | Q |
| 43 | F |
| 44 | S |
| 51 | R |
| 52 | T |
| 56 | A |
| 61 | A |
| 71 | S |
| 72 | Y |
| 73 | S |
| 77 | G |
| 78 | T |
| 79 | M |
| 80 | E |
| 81 | A |
| 89 | C |

According to the invention, CDR variants are formed by replacing at least one CDR of humanized ALPHA-ACTININ-4 mAbs with a corresponding CDR from a human antibody. According to the invention, CDR variants in which one or more CDRs are replaced by a corresponding CDR from a human antibody retain biological activity that is substantially similar to the binding affinity of the parental ALPHA-ACTININ-4 mAb. Generally, the CDR variants of the invention have a binding affinity that is at least 25% of the binding affinity of the parental ALPHA-ACTININ-4 mAb, more preferably at least 50%, most preferably at least 75%.

The CDR variants that have a reduced immunogenicity when compared to ALPHA-ACTININ-4 mAbs may be formed by grafting all six (three heavy chain and three light chain) CDRs from the ALPHA-ACTININ-4 mAbs of the present invention onto the variable light ($V_L$) and variable heavy ($V_H$) frameworks of human mAbs. However, less than all six of the CDRs of the ALPHA-ACTININ-4 mAbs of the present invention may be present, while still permitting the humanized antibody to retain activity. Only residues that are directly involved in antigen contact, the Specificity Determining Residues (SDRs), are needed. SDR variants are formed by replacing at least one SDR of the ALPHA-ACTININ-4 mAb with a residue at a corresponding position from a human antibody. It should be noted that not all CDRs include SDRs.

In a preferred embodiment, the variants of the present mAbs include a combination of CDR and/or SDR substitutions to generate variants having reduced immunogenicity and a binding affinity that is substantially similar to that of the parental mAb to ALPHA-ACTININ-4.

In addition to variants specifically described herein, other "substantially homologous" modified immunoglobulins can be readily designed and manufactured using various recombinant DNA techniques well known to those skilled in the art. For example, the framework regions (FWRs) can be varied at the primary structure level. Moreover, a variety of different human framework regions may be used singly or in combination as a basis for the variant. In general, modifications of the genes may be readily accomplished by a variety of well-known techniques, such as site-directed mutagenesis.

Alternatively, polypeptide fragments comprising only a portion of the primary antibody structure may be produced wherein the fragment substantially retains the immunoreactivity properties of the variant. These polypeptide fragments include fragments produced by proteolytic cleavage of intact antibodies by methods well known in the art, or fragments produced by inserting stop codons at the desired locations nucleotide sequence using site-directed mutagenesis. Single chain antibodies and fusion proteins which include at least an immunoreactivity fragment of the variant are also included within the scope of the invention.

The antibodies and their variants in accordance with the present invention may be directly or indirectly attached to effector moieties having therapeutic activity. Suitable effector moieties include cytokines, cytotoxins, radionuclides, drugs, immunomodulators, therapeutic enzymes, anti-proliferative agents, etc. Methods for attaching antibodies to such effectors are well known in the art. These conjugated antibodies may be incorporated into pharmaceutical compositions for use in treating diseases characterized by the expression of ALPHA-ACTININ-4, including cancer, such as cancer of the breast, ovary, head/neck, and brain. The pharmaceutical compositions are preferably administered to a mammal, more preferably a human patient, in order to treat the disease.

3. Methods of Producing ALPHA-ACTININ-4 mAbs

The ALPHA-ACTININ-4 mAbs of the present invention can be produced by generating murine hybridomas which produce mAbs specific for ALPHA-ACTININ-4. These hybridomas may be formed by the fusion of a mouse fusion partner cell and spleen cells from mice immunized against ALPHA-ACTININ-4. Mice may be immunized with crude or semi-purified preparations containing the antigens of interest. To immunize the mice, a variety of different conventional protocols may be followed. For example, mice may receive primary and boosting immunizations of antigenic preparations.

The cell fusions are accomplished by standard procedures well known to those skilled in the field of immunology. Fusion partner cell lines and methods for fusing and selecting hybridomas and screening for mAbs are well known in the art.

The mAbs of the present invention may be produced in large quantities by injecting hybridoma cells secreting the antibody into the peritoneal cavity of mice and, after appropriate time, harvesting the ascites fluid which contains a high titer of the mAb, and isolating the mAb therefrom. Alternatively, the mAbs may be produced by culturing hybridoma cells in vitro and isolating the secreted mAb from the cell culture medium.

The ALPHA-ACTININ-4 mAbs of the present invention, and chimeric or humanized variants thereof, can also be produced by expressing the appropriate DNA sequence in a host after the sequence has been operably linked to (i.e., positioned to ensure the functioning of) an expression control sequence. Such expression vectors are typically replicable in a host organism either as episomes or as an integral part of the host chromosomal DNA. The expression vectors typically contain expression control sequences compatible with the host cell, such as an origin of replication. In addition, the expression vector will typically include a promoter to control expression of the gene, optionally, with operator sequences, and have ribosome binding site sequences and the like for initiating and completing transcription and translation. Suitable promoters include the polyhedrin promoter, lactose promoter system, a tryptophan promoter system, a beta-lactamase promoter system, or a promoter system from phage lambda. Expression vectors may also contain selection markers. DNA sequences encoding the light chain and heavy chain of the ALPHA-ACTININ-4 mAbs may be inserted into separate expression vectors, or into the same expression vector.

Suitable hosts include prokaryotic strains such as *E. coli*; Bacilli, including *Bacillus subtilis*; enterobacteriacae, including *Salmonella, Serratia* and *Psuedomonas*. Suitable hosts also include eukaryotic hosts such as yeast, including *Saccharomyces; Pichia pastoris*; Sf9 insect cells; Sp2/0, VERO and HeLa cells, Chinese hamster ovary (CHO) cell lines; W138, BHK, COS-7 and MDCK cell lines. Other suitable hosts may also be used in accordance with known expression techniques.

The vectors containing the DNA segments of interest can be transferred into the host cell by well-known methods, which vary depending on the type of cellular host. For example, calcium chloride transfection, calcium phosphate treatment, electroporation or cationic liposome mediated transfection (such as DOTAP). Successfully transformed cells, can be identified by a variety of techniques well known in the art for detecting the binding of a receptor to a ligand.

Once expressed, the gene products can be purified according to standard methods in the art, including ammonium sulfate precipitation, affinity columns, column chromatography, and gel electrophoresis. Substantially pure immunoglobulins of at least 80% homogeneity are preferred, with about 90% to about 95% homogeneity being more preferred, and 98% to 99% or more homogeneity is most preferred, and is generally considered acceptable for pharmaceutical uses.

4. Methods of Using ALPHA-ACTININ-4 mAbs

Once purified, the ALPHA-ACTININ-4 mAbs, which may include any or all of the mAbs specific for ALPHA-ACTININ-4-related gene products, and/or chimeric, humanized, or other variants thereof, may be used therapeutically, or in developing and performing assays, in vivo or in vitro diagnostic procedures, and imaging. The antibodies can be used alone or in combination with a pharmaceutically-acceptable carrier formulation. Typically, the ALPHA-ACTININ-4 mAbs are incorporated into a pharmaceutically acceptable, non-toxic, sterile carrier as a suspension or solution. They can be used as separately administered compositions or given in conjunction with chemotherapeutic or immunosuppressive agents.

The present invention provides therapeutic and/or diagnostic compositions comprising an antibody molecule of the present invention in combination with a pharmaceutically acceptable excipient, diluent or carrier. The present invention also provides a process for preparation of a therapeutic and/or diagnostic composition comprising admixing an antibody molecule of the present invention together with a pharmaceutically acceptable excipient, diluent or carrier. The antibody molecule may be the sole active ingredient in the therapeutic or diagnostic composition, or may be accompanied by other active ingredients including other antibody ingredients, for example anti-T cell, anti-IFNγ or anti-LPS antibodies, or non-antibody ingredients such as xanthines. These compositions may be incorporated into kits for diagnosing and/or treating diseases characterized by the expression of ALPHA-ACTININ-4, including cancer, particularly solid tumors of the breast, ovary, head/neck, and brain.

The present invention also provides a method of treating human or animal subjects suffering from or at risk of a cancer that expresses ALPHA-ACTININ-4, such as solid tumors of the breast, ovary, head/neck, and brain, the method comprising administering to the subject a therapeutically effective amount of an antibody of the present invention, or a pharmaceutical composition comprising a therapeutically effective amount of an antibody of the present invention.

The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective dose can be estimated initially either in cell culture assays or in animal models, usually in rodents, rabbits, dogs, pigs, or primates. The animal model may also be used to determine the appropriate concentration range and route of administration. Such information can then be used to determine useful doses and routes for administration in humans.

The precise effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, an effective dose will be from 0.01 mg/kg to 50 mg/kg, preferably 0.1 mg/kg to 20 mg/kg, more preferably from about 1 mg/kg to about 15 mg/kg.

Compositions may be administered individually to a patient or may be administered in combination with other agents, drugs or hormones. According to some embodiments, the antibodies may be conjugated with these agents. A summary of the ways in which the antibodies of the present invention may be used therapeutically includes direct cytotoxicity by the antibody, either mediated by complement or by effector cells, or conjugated to anti-tumor drugs, toxins, and radionuclides. The antibodies can also be used for ex vivo removal of tumor cells from the circulation or from bone marrow.

Cytotoxic proteins may include, but are not limited to, Ricin-A, *Pseudomonas* toxin, Diphtheria toxin, and tumor necrosis factor. Diagnostic radionucleotides and cytotoxic agents such as cytotoxic radionuclides, drug and proteins may also be conjugated to the antibodies of the present invention. Examples of radionuclides which can be coupled to antibodies and selectively delivered in vivo to sites of antigen include $^{212}$Bi, $^{131}$I, $^{186}$Re, and $^{90}$Y, among others. The radionuclides exert their cytotoxic effect by locally irradiating the cells, leading to various intracellular lesions, as is known in the art of radiotherapy. Examples of cytotoxic drugs which can be conjugated to antibodies and subsequently used for in vivo therapy include, but are not limited to, daunorubicin, doxorubicin, methotrexate, and Mitomycin C. Cytotoxic drugs interface with critical cellular processes including DNA, RNA, and protein synthesis.

The dose at which the antibody molecule of the present invention is administered depends on the nature of the condition to be treated, and on whether the antibody molecule is being used prophylactically or to treat an existing condition. If administered prophylactically, i.e., as a vaccine, the antibody is administered in an amount effective to elicit an immune response in the subject.

If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, per week or even once every 1 or 2 months.

A pharmaceutical composition may also contain a pharmaceutically acceptable carrier for administration of the antibody. The carrier should not itself induce the production of antibodies harmful to the individual receiving the composition and should not be toxic. Suitable carriers include those known in the art, and may be selected from large, slowly metabolized macromolecules such as proteins, polypeptides, liposomes, polysaccharides, polylactic acids, polyglycolic acids, polymeric amino acids, amino acid copolymers and inactive virus particles, although suitable carriers are not limited to these examples.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous, subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain additional agents which protect the antibody from degradation but which release the antibody once it has been absorbed from the gastrointestinal tract. Such additional agents are well-known to those skilled in the art.

It is also envisaged that the antibodies of the present invention may also be administered in methods of conducting gene therapy. In order to achieve this, DNA sequences encoding the heavy and light chains of the antibody molecule under the control of appropriate DNA components are introduced into a patient such that the antibody chains are expressed from the DNA sequences and assembled in situ.

The antibody molecule of the present invention may also be used in diagnosis of diseases characterized by the expression of ALPHA-ACTININ-4, such as cancer. For example, in vivo diagnosis and imaging of a solid tumor of the breast, ovary, head/neck, and/or brain that expresses ALPHA-ACTININ-4 may be performed in accordance with the methods of the invention. The antibody molecules of the present invention may also be used for diagnosis in vitro, for example, by using a kit including the antibody molecules to detect the presence of the cancer marker ALPHA-ACTININ-4 in a fluid or tissue sample.

In diagnosis, the antibodies may be used in immunoassays to screen body fluids, such as serum, plasma, sputum, effusions, urine, cerebrospinal fluid, and the like, for the presence of ALPHA-ACTININ-4. The antibodies may be used for scanning or radioimaging, when labeled with an appropriate radiolabel, to detect primary or metastatic foci of tumor cells. Furthermore, the antibodies are useful in lymphoscintigraphy to detect lymph node involvement in the disease.

The antibodies of the present invention are also useful for immunopathological analysis, such as the differential diagnosis of tumor type, and the subclassification of the tumor based on its expression of ALPHA-ACTININ-4. Such determinations may be important in assessment of metastatic potential, predicted responses to therapy, and overall prognosis.

In particular, because of the specificity of the ALPHA-ACTININ-4 mAbs of the present invention, they may permit the definition of subpopulations of tumor cells among the heterogeneous cells present in a growing tumor. These antibodies could be used, for example, in the typing and cross-matching of the tumor cell "lines" comprising the tumor by means of flow cytometry, both at the time of surgery and prior to therapy. An analysis of the tumor cell subpopulations with the antibodies of this invention, and a battery of additional mAbs, may be used to define (a) which antigen preparation would be the most appropriate for specific active immunotherapy, (b) which mAb or chimeric antibody would be efficacious for the particular cancer; and (c) which antibody or combination of mAbs should be used for imaging the patient at a later date in search for recurrent or metastatic tumors. Additional diagnostic and therapeutic uses for the ALPHA-ACTININ-4 mAbs of the present invention are also envisioned.

For diagnostic purposes, the antibodies may either be labeled or unlabeled. Unlabeled antibodies can be used in combination with other labeled antibodies (second antibodies) that are reactive with the humanized antibody, such as antibodies specific for human immunoglobulin constant regions. Alternatively, the antibodies can be directly labeled. A wide variety of labels can be employed, such as radionuclides, fluors, enzymes, enzyme substrates, enzyme cofactors, enzyme inhibitors, ligands (particularly haptens), etc. Numerous types of immunoassays are available and are well known to those of skill in the art.

The antibodies of the present invention are useful for immunoassays which detect or quantitate ALPHA-ACTININ-4 or cells bearing ALPHA-ACTININ-4 in a sample. Such an immunoassay typically comprises incubating a biological sample in the presence of a detectably labeled antibody of the present invention capable of identifying the tumor antigen, and detecting the labeled antibody which is bound in a sample.

In an aspect of the present invention the level, localization or both of one or more forms of ALPHA-ACTININ-4 can determine, confirm or indicate the status of a cell, collection of cells, or sample from a subject. As used herein, "confirm" means that based on the level, localization or both of one or more forms of ALPHA-ACTININ-4 in a cell, collection of cells or sample, subject etc provides a sufficient basis to characterize the status of a cell, collection of cells, sample or subject etc. As used herein, "indicate" means that based on the level, localization or both of one or more forms of ALPHA-ACTININ-4 in a cell, collection of cells or sample, subject etc provides that more likely than not or greater probability of determining the status of a cell, collection of cells, sample or subject etc. is of a particular status. For example, detecting a greater amount or stronger staining of an ALPHA-ACTININ-4 antigen detected by Alper-ALPHA-ACTININ-4 mAb indicates increased likelihood of survival in a patient suspected of or having breast cancer.

A status of a cell or collection of cells can include any aspect and in one aspect is whether that a cell, collection of cells, sample, etc. are metastatic, non-metastatic tumor cells or normal cells. A status of a subject can include whether the analysis provides information on likelihood of survival of the subject. For example, the overall survival rate of breast cancer patients with strong staining for an ALPHA-ACTININ-4 antigen detected by Alper-ALPHA-ACTININ-4 mAb expression is significantly higher than patients with no staining or weak staining of the same ALPHA-ACTININ-4 antigen.

Examples of confirmatory analysis, assays, tests etc. that can be used to confirm or in combination with those disclosed include, without limitation, those set forth in Alper, US Publication No. 2008/0293162 (herein incorporated by reference in its entirety) as well as histological examination of samples.

In an aspect of the present invention the level, localization or both of one or more forms of ALPHA-ACTININ-4 is diagnostic or prognostic of a disease or outcome probability. In an aspect, detecting a greater amount or stronger staining of nuclear, soluble or nuclear and soluble ALPHA-ACTININ-4 antigen indicates increased likelihood of survival in a patient suspected of or having breast cancer.

In an aspect of the present invention a reduced level of a soluble form of PCPB-1 in a cell, collection of cells or sample can diagnose, prognose, monitor, determine, confirm or indicate that such derived is from a metastatic tissue. In one aspect, "reduced" can mean reduced relative to a control, with the control being a normal cell of the same type that is non-metastatic. In this aspect, the reduction can be greater than 10, 20, 30, 40, 50, 60, 70, 80, 90, 95, or 99%. In another aspect, the reduction can be two-, four-, ten-, or twenty-fold or more.

In an aspect of the present invention an increased level of a soluble form of PCPB-1 in a cell, collection of cells or sample can diagnose, prognose, monitor, determine, confirm or indicate that such derived is from a metastatic tissue. In one aspect, "increased" can mean increased relative to a control, with the control being a normal cell of the same type that is non-metastatic. In this aspect, the increase can be greater than 10, 20, 30, 40, 50, 60, 70, 80, 90, 95, or 99%. In another aspect, the increase can be two-, four-, ten-, or twenty-fold or more.

In one aspect of the present invention, ALPHA-ACTININ-4 expression is measured using immunohistochemistry followed by a quantitative method. In one aspect, a quantitative method can be software such as AQUANALYSIS™ software (manual is herein incorporated by reference in its entirety) (HistoRx, Inc., New Haven, Conn., USA). In another aspect, a quantitative method such as AQUANALYSIS™ software can be used in addition to the methods described in Example 5.

In one aspect of the present invention, ALPHA-ACTININ-4 expression is relative to ALPHA-ACTININ-4 expression in healthy controls patients or healthy cells samples from a patient. In another aspect, ALPHA-ACTININ-4 expression in cancer cells can be expressed as a percentage of ALPHA-ACTININ-4 expression in normal controls. Statistical significance of differences in ALPHA-ACTININ-4 expression can be measured using the Student's t-test. In one aspect, t=0.99. In another aspect, t=0.95. In another aspect, t=0.90.

In one aspect of the present invention, "strong expression" of ALPHA-ACTININ-4 can be at least a 3-fold, 4-fold, 5-fold or greater increase in ALPHA-ACTININ-4 expression as compared to normal tissues. This may be indicated as "strong staining" or a "3" in a quantitative scoring method on a scale of 0-3. In another aspect, "moderate expression" or "intermediate expression" of ALPHA-ACTININ-4 can be at least a 2- to 3-fold increase in ALPHA-ACTININ-4 expression as compared to normal tissues. This may be indicated as a "2" in a quantitative scoring method on a scale of 0-3.

In another aspect, "weak expression" of ALPHA-ACTININ-4 can be a greater than the ALPHA-ACTININ-4 expression as compared to normal tissues but less than a 2-fold increase in ALPHA-ACTININ-4 expression as compared to normal tissues. This may be indicated as a "1" in a quantitative scoring method on a scale of 0-3. In another aspect, "no staining" of ALPHA-ACTININ-4 can be the same as ALPHA-ACTININ-4 expression compared to tissues or cells not treated with antibody, or another similar control, i.e. not above background. This may be indicated as a "0" in a quantitative scoring method on a scale of 0-3. In an aspect, a immunohistochemistry score is assigned as a percentage of positive tumor cells (the number of positive tumor cells over the total number of tumor cells). In an aspect, at least 20 cells must be considered to be scored.

In another aspect of the present invention, increases in ALPHA-ACTININ-4 expression can be expressed as increases in cells or tissues as a whole. In another aspect, greater ALPHA-ACTININ-4 expression can be expressed as an increase in the nuclear staining of cells. In another aspect, increases in ALPHA-ACTININ-4 expression can be expressed as increases in the total amount of ALPHA-ACTININ-4 expression in a cell.

In another aspect of the present invention, decreases in ALPHA-ACTININ-4 expression can be expressed as decreases in cells or tissues as a whole. In another aspect, decreases in ALPHA-ACTININ-4 expression can be expressed as decreases in the cytoplasm of cells. In another aspect, decreases in ALPHA-ACTININ-4 depression can be expressed as increases or decreases in the plasma of a patient.

In one aspect of the present invention, ALPHA-ACTININ-4 expression in breast cancer cells can be greater as compared to ALPHA-ACTININ-4 expression in normal breast cells. In another aspect, breast cancer cells can exhibit weak ALPHA-ACTININ-4 expression, while normal breast cells can exhibit relatively strong nuclear or soluble ALPHA-ACTININ-4 expression.

In an aspect of the present invention a similar level of a soluble form of ALPHA-ACTININ-4 in a cell, collection of cells or sample to a normal control can diagnose, prognose, monitor, determine, confirm or indicate that such cell was derived from a non-metastatic tissue.

In an aspect of the present invention, a lack of localization of a soluble form of PCPB-1 in a cell nucleus can diagnose, prognose, monitor, determine, confirm or indicate that such derived is from advanced breast cancer tissue.

In an aspect of the present invention, the cell, collection of cells or sample is a cervical or breast cell collection of cells or sample.

Antibodies and antibody fragments of the present invention are also useful for immunopathological analysis, such as the differential diagnosis of tumor type, and the subclassification of the tumor based on its expression of ALPHA-ACTININ-4 antigens detected by Alper-ALPHA-ACTININ-4 mAbs, including, without limitation, assessment of metastatic potential, predicted responses to therapy, and overall prognosis or survival. In an aspect of the present invention, there is an association of nuclear overexpression of ALPHA-ACTININ-4 antigen detected by Alper-ALPHA-ACTININ-4 mAb with overall survival in breast cancer patients. In this aspect, an immunoassay using a mAb of the present invention can detect nuclear overexpression of an ALPHA-ACTININ-4 antigen detected by Alper-ALPHA-ACTININ-4 mAb and can indicate or confirm an estimate of survival time for breast cancer patients.

In another aspect, high expression in breast cancer tissues of ALPHA-ACTININ-4 antigens detected by Alper-ALPHA-ACTININ-4 mAb is correlated with high membrane HER2 expression in breast cancer tissues. In this aspect, "correlated" indicates a statistical probability less than 0.05.

ALPHA-ACTININ-4 antibodies and antibody fragments permit the definition of subpopulations of tumor cells among the heterogeneous cells present in a growing tumor and can be used, for example, in the typing and cross-matching of the tumor cell "lines," including, without limitation, by means of flow cytometry, both at the time of surgery and prior to therapy. An analysis of the tumor cell populations or subpopulations with antibodies or antibody fragments of this invention, and a battery of additional antibodies or antibody fragments, can be used to define (a) which antigen preparation would be the most appropriate for specific active immunotherapy, (b) which antibody or antibody fragment or chimeric antibody would be efficacious for the particular cancer; and (c) which antibody or combination of antibodies or antibody fragments should be used for imaging the patient at a later date in search for recurrent or metastatic tumors.

Thus, in this aspect of the invention, a biological sample may be treated with nitrocellulose, or other solid support or carrier which is capable of immobilizing cells, cell particles or soluble proteins or glycoproteins. The support may then be washed with suitable buffers followed by treatment with the detectably labeled antibody of the present invention. The solid phase support may then be washed with the buffer a second time to remove unbound antibody. The amount of bound label on said solid support may then be detected by conventional means.

One of the ways in which the antibody of the present invention can be detectably labeled is by linking the same to an enzyme and use in an enzyme immunoassay (EIA) or enzyme-linked immunosorbent assay (ELISA). This enzyme, when subsequently exposed to its substrate, will react with the substrate generating a chemical moiety which can be detected, for example, by spectrophotometric, fluorometric or by visual means. In an alternate embodiment, the enzyme is used to label a binding partner for the antibody of the invention. Such a binding partner may be an antibody against the constant or variable region of the antibody of the invention, such as a heterologous anti-mouse immunoglobulin antibody. Alternatively, the binding partner may be a non-antibody protein capable of binding to the antibody of the present invention.

By radioactively labeling the antibodies of the present invention, it is possible to detect ALPHA-ACTININ-4 through the use of a radioimmunoassay (RIA). The radioactive isotope can be detected by such means as the use of a gamma counter or a scintillation counter or by autoradiography. Isotopes which are particularly useful for the purpose of the present invention are well known in the art.

It is also possible to label the antibodies of the present invention with a fluorescent compound. When the fluorescently labeled antibody is exposed to light of the proper wavelength, its presence can then be detected due to fluorescence. The antibodies of the present invention also can be detectably labeled by coupling to a chemiluminescent compound. The presence of the chemiluminescently labeled antibody is then determined by detecting the presence of luminescence that arises during the course of a chemical reaction. A bioluminescent compound may also be used to label the antibodies of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase and sequorin.

Detection of the antibody, fragment or derivative may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

In situ detection may be accomplished by removing a specimen from a patient, and providing the labeled antibody, or the unlabelled antibody plus a labeled binding partner to such a specimen. Through the use of such a procedure, it is possible to determine not only the presence of the antigen but also its distribution in the examined tissue. Using the present invention, those of ordinary skill will readily perceive that any of a wide variety of histological methods (such as staining procedures) can be modified in order to achieve such in situ detection. Such methods include, for example, immunohistochemical staining procedures. In a preferred embodiment, an avidin-biotin immunoperoxidase staining system can be used, and a kit utilizing this system is also contemplated, although the methods of the present invention may utilize any suitable staining procedures known in the art.

Kits according to the present invention may include frozen or lyophilized antibodies to be reconstituted by thawing or by suspension in a liquid vehicle. The kits may also include a carrier or buffer. Preferably, the kit also comprises instructions for reconstituting and using the antibody. The kit employing antibodies, including chimeric and humanized antibodies of the present invention, can be used for immunohistochemical evaluation of cancers, including cancer of the breast, ovary, head/neck, and brain.

The kits including the reagents necessary for immunohistochemical analysis may be provided as follows: a) an ALPHA-ACTININ-4 mAb of the present invention, or chimeric or humanized variants thereof; b) blocking reagent (in the form of, for example, goat serum) and secondary antibody (such as, for example, goat anti-mouse antibody); c) detectable marker (such as, for example, immunoperoxidase or alkaline phosphatase); and d) developing reagents. The primary antibody (Alper-ALPHA-ACTININ-4 mAb or variants thereof) serves as an antigen which can bind more than one secondary antibody. The secondary antibodies form a "bridge" between the primary antibody and the complex formed by the detectable marker and developing reagent (for example, a horseradish peroxidase-antiperoxidase complex).

Any suitable detection system may be used in accordance with the methods and kits of the present invention. Such detection systems are widely used in immunofluorescence applications, and may be imaged using techniques including, but not limited to, flow cytometry, microscopy, Western blotting, and ELISAs. Suitable detection systems may employ conjugates of secondary antibodies, conjugates of colloidal gold, or conjugates of secondary proteins, in order to amplify the signal from a primary protein (in the context of the present invention, the primary protein signal being amplified is bound a ALPHA-ACTININ-4 antibody, which may or may not be labeled, for example with a protein such as biotin), which is in turn being used to detect a specific target (in the context of the present invention, the target is a ALPHA-ACTININ-4 expression product).

Suitable secondary conjugates for use in the methods and kits of the present invention may include, but are not limited to, enzyme conjugates of a secondary antibody and an enzyme such as horseradish peroxidase or alkaline phosphatase; enzyme conjugates of avidin or streptavidin and an enzyme such as horseradish peroxidase or alkaline phosphatase; enzyme conjugates of protein A or protein G and an enzyme such as horseradish peroxidase or alkaline phosphatase; conjugates of colloidal gold and a secondary antibody; conjugates of colloidal gold and avidin or streptavidin; conjugates of magnetic particles and a secondary antibody; and conjugates of secondary antibodies and labels such as fluorescent dyes and biotin. The present invention is not limited to any particular detection systems, and it is considered within the ability of the person of ordinary skill in the art to utilize these or other detection systems in accordance with the present invention. These secondary conjugates (also referred to as labels in the context of the present invention) are useful for visualizing antigen-antibody complexes.

The antibody, fragment or derivative of the present invention may also be adapted for utilization in an immunometric assay, also known as a "two-site" or "sandwich" assay. In a typical immunometric assay, a quantity of unlabelled antibody (or fragment of antibody), is bound to a solid support that is insoluble in the fluid being tested and a quantity of detectably labeled soluble antibody is added to permit detection and/or quantitation of the ternary complex formed between solid-phase antibody, antigen, and labeled antibody.

For purposes of in vivo imaging of colon, breast, and ovarian cancer using the antibodies of the present invention, there are many different labels and methods of labeling known to those of ordinary skill in the art. Examples of the types of labels which can be used in the present invention include radioactive isotopes, paramagnetic isotopes, and compounds which can be imaged by positron emission tomography (PET). Those of ordinary skill in the art will know of other suitable labels for binding to the antibodies used in the invention, or will be able to ascertain such, using routine experiments. Furthermore, the binding of these labels to the antibody can be done using standard techniques common to those of ordinary skill in the art.

5. ALPHA-ACTININ-4 Expression Products as Drug Development Targets

In addition, the present invention relates to the discovery that ALPHA-ACTININ-4 and homologues thereof may cause the expression of a reduced amount of nuclear or soluble ALPHA-ACTININ-4 antigens by cells in patients suffering from various diseases, such as cancers, and more specifically solid tumors of the breast, ovary, head/neck, and brain, specifically breast. This expression of ALPHA-ACTININ-4 antigens presents a novel drug development target, and accordingly the present invention also relates to the use of such ALPHA-ACTININ-4 antigens as biomarkers that may be targeted not only by the ALPHA-ACTININ-4 mAbs of the present invention, but also by various other molecules, such as siRNA, antisense oligonucleotides, vaccines, and chemical compounds.

Methods for developing drugs useful in treating and/or diagnosing diseases characterized by the expression of gene products of ALPHA-ACTININ-4 and homologues thereof may include the steps of identifying the gene products expressed by ALPHA-ACTININ-4 and homologues thereof in a subject having a disease, and utilizing those gene products as to development and identify drugs that specifically target the gene products.

Once candidate drugs have been developed based on the ALPHA-ACTININ-4 antigens, the ALPHA-ACTININ-4 antigens and ALPHA-ACTININ-4 mAbs of the present invention may be used to aid in screening the various drug candidates, in order to identify those drug candidates that exhibit a desired level of specificity for diseased cells presenting ALPHA-ACTININ-4 expression products.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

EXAMPLES

Example 1

An 8% Tris-glycine gel shows recombinant ALPHA-ACTININ-4 protein, and soluble ALPHA-ACTININ-4 protein from KATO-3 conditioned cell medium isolated with Alper ALPHA-ACTININ-4 mAb.

Example 2

Protein obtained using Alper ALPHA-ACTININ-4 mAb is digested with trypsin and analyzed by MALDI-MS. The major protein identified is ALPHA-ACTININ-4, SwissProt 56.8.

Example 3

Plasma samples (Control: plasma from healthy people, Breast Cancer: plasma from breast cancer patients) are obtained from control and patient groups and diluted with PBS at a ratio of 1:100. Plasma ALPHA-ACTININ-4 levels are measured with an enzyme-linked immunosorbent enzyme assay. The ELISA plates (Nalge NUNC International, Rochester, N.Y.) are coated with 100 μl/well of diluted plasma and incubated at 4° C. overnight. The blood plasma samples are analyzed in a blinded fashion. The wells are washed with PBS and incubated at room temperature for one hour with blocking buffer (5% BSA in PBS). After washing with PBS, the primary antibody, Alper-ALPHA-ACTININ-4 is added in dilution buffer (45 μg/ml) (PBS buffer, 1% BSA, 0.01% Tween-20). The wells are washed with PBS/0.03% Tween-20 and incubated at room temperature for one hour with 100 μl/well secondary antibody (HRP-Donkey anti-mouse IgG, Jackson ImmunoResearch, West Grove, 1000 PA) diluted 1:3000. After washing the wells, 100 μl Immunopure TMB substrate solution (Pierce, Rockford, Ill.) is added. Color reaction is stopped by the addition of 100 μl/well 1N $H_2SO_4$ and the analysis was performed with an ELISA Reader. The figures represent optical density (OD) values of plasma readings for ALPHA-ACTININ-4 levels.

Example 4

Immunohistochemistry is performed according to Example 5 on a total of 714 breast tumor and control samples are obtained from Yale School of Medicine, Department of Pathology, Tissue Microarray and Archiving, YTMA 49. Of these samples, 630 were from female breast cancer patients. Available patient characteristics are examined for any association with overall survival time using the long rank test for categorical factors, and Cox's proportional hazards regression for continuous variables as well as for multiple variables for their combined effect on survival. Overall survival is measured as the number of months from diagnosis to death or last contact. Patients without dates of death were censored on their date of last contact. Nuclear grade is omitted from multivariable analyses due to the number of samples missing this information. Non-significant variables are removed one at a time until all variables in the model were significant at the 0.05 level. Kaplan-Meier plots present the estimated survival for measures of ACT4 and for categorical variables remaining significant in the mode. Of note, factors of stage and histology are not available for most the samples, so are not included in any survival models.

Figure 3:
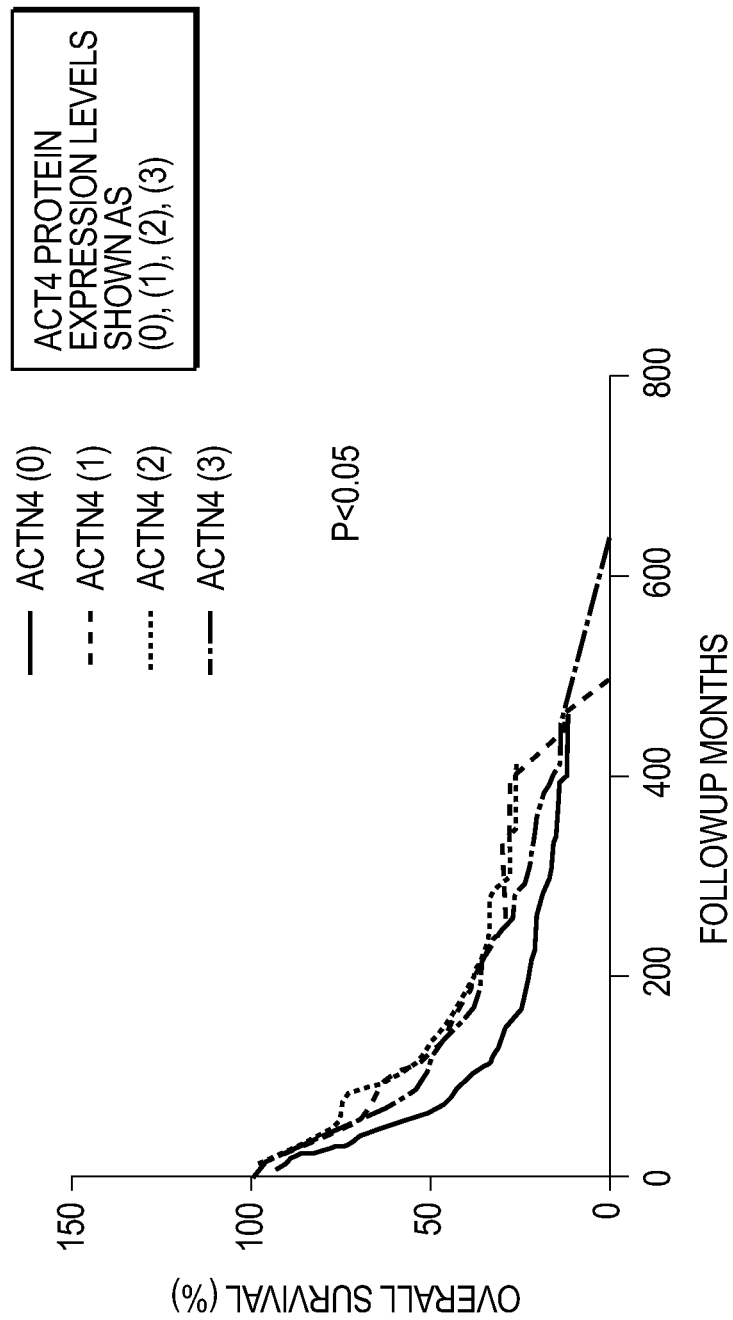
FIG. 3. ALPHA-ACTININ-4 (ACT4) protein expression in a 700 breast cancer patient cohort from Yale University.

When all factors are included in a Cox regression model, age ($p<0.001$), race ($p=0.026$), nodal status ($p<0.001$), and Alper-ACT4 ($p<0.05$) are the only factors that remain significantly associated with survival time in combination. Higher nuclear Alper-ALPHA-ACTININ-4 mAb score is associated with longer survival. FIG. 3 presents the overall survival curves for Alper-ALPHA-ACTININ-4 mAb. All patients have died or have last follow-up by 500 months except for one patient who died after 660 months. Intensity of ALPHA-ACTININ-4 antigen (ACT4 or ACTN4 Protein) staining is indicated using a quantitative scoring method: "0" equals no staining, "1" equals weak staining, "2" equals intermediate staining, and "3" equals strong staining.

Example 5

Actinin-4 IHC Kit is a sensitive immunohistochemistry kit that is specific for the detection of Actinin-4 protein in formalin fixed, paraffin-embedded (FFPE) tissue sections. Alper Anti-actinin-4 monoclonal antibody recognizes N-terminal and the native form of Actinin-4.

Reagents Provided in the Kit from ALPER BIOTECH, Cat. No. AB02

The materials listed are sufficient for 20 tests. The number of tests is based on the use of 200 μL each of ready-to-use reagent per slide.

Retrieval Buffer (10×)
30 mL, Citrate Buffer (pH6.0)
Dilute at 1:10 using distilled or deionized water prior to staining; unused working solution may be stored at room temperature.
Wash Buffer (10×)
30 mL, Tris buffered saline with Tween 20 (pH7.6)
Dilute at 1:10 using distilled or deionized water prior to staining; unused working solution may be stored at room temperature (20-25° C.).
Peroxidase Blocking Buffer
5 mL, 3% Hydrogen Peroxide
Ready-to-use
Blocking Reagent,
4 mL
Ready-to-use
Human Actinin-4 Monoclonal Mouse IgG2 antibody
500 μg/mL; 100 μl total (50 μg)
Dilute in Antibody Diluents immediately before use (recommend use at 1:800-1:3000 dilution)*.
  *Note: For Yale Pathology/Yale Cancer Center Tissue arrays, the optimal concentration of Actinin-4 antibody is 1:3000; for all other source of tissue sections or arrays, 1:800 is recommend as a starting concentration for optimization.
Antibody Diluents
5 mL
Ready-to-use
MACH3 Mouse Probe
4 mL, Biocare Medical; Cat No. M3M530
Ready-to-use
MACH3 Mouse HRP Polymer
4 mL, Biocare Medical; Cat No. M3M530
Ready-to-use
DAB Chromogen
0.2 mL, Diaminobenzedinetetrahydrochloride (DAB) substrate solution
Before use, add 20 μL DAB substrate solution to 1 mL of substrate buffer. The prepared Substrate working solution should be stored at 2-8° C. and used within 5 days.
Do not expose DAB components to direct or bright light during storage and staining process.
DAB substrate buffer 5 mL
Ready-to-use Materials Required but not Included in the Kit Reagents:
  Xylene
  Ethanol
  Hematoxylin
  Permanent mounting media
  Distilled or deionized water Lab Equipment:
  Steamer or microwave oven or domestic steel pressure cooker (for antigen retrieval)
  General lab equipment for immuno-histostaining such as slide racks, staining jars, forceps, cover slips, timer, pipettes, etc.
  Microscope equipment and accessories Storage and Stability Store Actinin-4 IHC Kit at 2-8° C. The kit is stable for one year at 4° C. Do not use after expiration date.

Precautions

Take reasonable precautions when handling reagents. Use disposable gloves when handling suspected carcinogens or toxic materials (examples: DAB, xylene). Unused solution should be disposed of according to applicable local, state and federal regulations.

Staining Protocol

The Actinin-4 Immunohistostaining Kit has been designed for the staining of tissues that have been fixed (usually in neutral buffered formalin) and subsequently embedded in paraffin before sectioning. The protocol written here is optimized for specific Actinin-4 protein staining and was developed using a breast cancer tissue microarray and process guidelines provided by The Yale Pathology/Yale Cancer Center Tissue Microarray Facility.

This protocol is recommended as a starting point. Whenever using a new antibody or immunohistochemistry kit, optimization by the individual end-user may be required.

Note:
  All reagents should be allowed to equilibrate to room temperature (20-25° C.) before use, and the whole staining process should be performed at room temperature except for the steps specifically described below.
  Do not allow specimens to dry during the staining procedure. Specimen drying may cause increased non-specific staining and background.
  Some tissue arrays may need to bake to remove over-covered paraffin prior to the procedure. Check tissue array manufacturer's instruction. If needed, bake at 55-60° C. for 30 minutes.

Deparaffinization and Rehydration

Prior to staining, tissue sections must be deparaffinized and rehydrated. Incomplete removal of paraffin can cause poor staining of the section.

Step 1. Immerse slides in xylene and incubate for 15 minutes. Repeat once with fresh xylene for another 15 minutes.
Step 2. Immerse slides in xylene:ethanol (1:1) for 5 minutes.
Step 3. Immerse slides in 100% ethanol for 5 minutes, and follow with immersion in 95%, 75% and 50% ethanol for 3 minutes each.
Step 4. Rinse slides with reagent-quality water for 5 minutes; keep in water until ready to perform antigen retrieval.

Heat Induced Antigen Retrieval (HIAR)

Most formalin-fixed tissue requires an antigen retrieval step before immunohistochemical staining can proceed. Heat induced antigen retrieval can be performed using a steamer, pressure cooker, or a microwave. The retrieval time written in this protocol is based on using a retrieval steamer. The heating time may need to be adjusted if you use a different device and method.

Step 1. Fill plastic Coplin jar/container with Retrieval Buffer.
Step 2. Place the Coplin jar/container in steamer.
Step 3. Turn on steamer and preheat to 90-100° C. Carefully put slides into the Coplin jar/container and steam for 40 min (95-100° C.).
Step 4. Turn off the steamer, remove the Coplin jar, place at room temperature and allow slides to cool for 20 min.
Step 5. Rinse slide by incubation of slide in wash buffer for 3 minutes. Repeat this step twice and begin staining procedure.

Staining Procedure

Step 1. Tap off excess washing buffer. Apply enough Peroxidase Blocking Buffer to cover specimen, and incubate for 5 minutes.
Step 2. Rinse slide by incubation of slide in with wash buffer for 3 minutes. Repeat this step twice with fresh buffer.
Step 3. Tap off excess washing buffer. Apply enough Blocking Reagent to cover specimen and incubate for 5 minutes.
Step 4. Rinse slide by incubation of slide in with wash buffer for 3 minutes. Repeat this step twice with fresh buffer.
Step 5. Tap off excess washing buffer. Apply enough anti-Actinin-4 antibody (recommend 1:3000 dilution in antibody diluents) to cover specimen, and incubate for 1 hour.
Step 6. Rinse slide by incubation of slide in with wash buffer for 3 minutes. Repeat this step twice with fresh buffer.
Step 7. Tap off excess washing buffer. Apply enough Mach3 probe to cover specimen, and incubate for 15 minutes.
Step 8. Rinse slide by incubation of slide in wash buffer for 3 minutes. Repeat this step twice with fresh buffer.
Step 9. Tap off excess washing buffer. Apply enough Mach3 polymers to cover specimen, and incubate for 15 minutes.
Step 10. Rinse slide by incubation of slide in wash buffer for 3 minutes. Repeat this step twice with fresh buffer.
Step 11. Tap off excess washing buffer. Apply enough DAB substrate solution to cover specimen and incubate until desired stain intensity develops.
Step 12. Rinse slide in tap water for 3 minutes.
Step 13. If desired, complete counterstain (See instruction for hematoxylin counterstaining) Rinse to clear.
Step 14. Immerse slides in 70%, 80%, 95%, 100% ethanol for 2 minutes each, and follow in xylene for 2 minutes twice.
Step 15. Dry and mount slides.

Instruction for Hematoxylin Counterstain

Step 1. Immerse slides in hematoxylin solution. Incubate for 30 seconds to 5 minutes, depending on the strength of hematoxylin used.
Step 2. Rinse to clear with tap water and continue by dehydration from Step 14.

Troubleshooting

| Problems | | Possible Causes | Solutions |
| --- | --- | --- | --- |
| Weak or no staining | 1. | The primary antibody concentration is too low. | The concentration of the primary antibody can be increased from 1:3000 up to 1:800 depending on the tissue section source. |
| | 2. | Incomplete removal of paraffin | |

| Problems | Possible Causes | Solutions |
|---|---|---|
| | 3. Tissues over-fixation<br>4. Not efficient antigen retrieval<br>5. Reagents not used in proper order or omitted steps<br>6. Expired antibody or reagents | Deparaffinize sections longer or change to fresh xylene; some tissue array may need to bake to remove over-covered paraffin.<br>Increasing the concentration of primary antibody to 1:500; if this does not work, reduce duration of post-fixation.<br>Adjust antigen retrieval time based on the situation of section fixation and retrieval device you used.<br>Review notes and procedure used.<br>Check kit expiration dates and kit storage condition |
| Over staining | 1. Too high concentration of primary antibody, or too high temperature when doing staining<br>2. Too long incubation time of DAB substrate.<br>3. Slide dried during staining process | Depending on tissue sections, the concentration of primary antibody can be diluted; Check the room temperature range is at 20-25° C. when doing staining.<br>Reduce incubation time of DAB substrate<br>Avoid sections to dry during staining process. |
| High background | 1. Incomplete removal of paraffin<br>2. Sections dried during staining process<br>3. Slide not rinse thoroughly<br>4. Antigen over-retrieval | Deparaffinize sections longer or change fresh xylene.<br>Do not allow sections to dry during staining process; use humid container during incubation of primary antibody.<br>Use fresh solution in buffer jars; rinse at least three times between steps.<br>Optimize antigen retrieval time if you used microwave or pressure cooker for retrieval. |

What is claimed is:

1. An isolated antibody or antibody fragment that binds ALPHA-ACTININ-4, comprising a heavy chain variable domain comprising three complementary determining regions (CDRs) comprising the amino acid sequences of SEQ ID NO: 2, SEQ ID NO: 3, and SEQ ID NO: 4, and a light chain variable domain comprising three CDRs comprising the amino acid sequences of SEQ ID NO: 6, SEQ ID NO: 7; and SEQ ID NO: 8.

2. The antibody or antibody fragment according to claim 1 wherein said ALPHA-ACTININ-4 is a soluble protein having a molecular weight of about 95 to 104 kilodaltons as measured by gradient polyacrylamide gel electrophoresis.

3. The antibody or antibody fragment according to claim 1, wherein the antibody or antibody fragment is immobilized on a solid phase.

4. The antibody or antibody fragment according to claim 1, wherein the antibody or antibody fragment is detectably labeled.

5. The antibody or antibody fragment according to claim 1, wherein the antibody or antibody fragment is conjugated to a cytokine, cytotoxin, radionuclide, drug, immunomodulator, therapeutic enzyme, anti-proliferative agent, cytotoxic radionuclide, cytotoxic drug, or cytotoxic protein.

6. The antibody or antibody fragment of claim 1 specific for a nuclear or soluble form of ALPHA-ACTININ-4.

7. The antibody or antibody fragment of claim 1, wherein the antibody or antibody fragment is humanized.

8. A pharmaceutical composition comprising the antibody or antibody fragment according to claim 1 in combination with a pharmaceutically acceptable carrier.

9. A recombinant nucleic acid encoding the antibody or antibody fragment of claim 1.

10. An isolated vector comprising the nucleic acid of claim 9.

11. An isolated host cell comprising the vector of claim 10.

12. An isolated antibody or antibody fragment produced by a method comprising culturing the host cell of claim 11, expressing the antibody or antibody fragment, and recovering the antibody or antibody fragment expressed by the host cell.

13. An immunoassay for detecting ALPHA-ACTININ-4 in a biological sample, comprising contacting said biological sample with the antibody or antibody fragment of claim 1, and the presence or absence of ALPHA-ACTININ-4 is determined by qualitatively or quantitatively detecting the presence or absence of an antibody bound to ALPHA-ACTININ-4.

14. The immunoassay of claim 13, wherein the biological sample comprises blood, tissue, or cells.

15. The immunoassay of claim 14, wherein the blood sample is whole blood, plasma, or serum.

16. The immunoassay of claim 14, wherein the tissue or cell is from breast, ovary, head, neck, or brain.

17. The immunoassay of claim 13, wherein the sample comprises circulating tumor cells.

18. A method for diagnosing breast cancer comprising: (a) obtaining a specimen from a human patient; (b) contacting the specimen with the antibody or antibody fragment of claim 1; (c) quantitatively determining whether the antibody or antibody fragment specifically binds to said specimen; (d) comparing the level of specific binding to a control, wherein binding at a level that is lower than the control indicates the presence of breast cancer in said specimen.

19. A kit comprising:
  i) the isolated antibody or antibody fragment of claim 1 and a secondary antibody that binds to the antibody or antibody fragment of claim 1, wherein the secondary antibody is conjugated to a detectable label; or
  ii) the isolated antibody or antibody fragment of claim 4; and instructions for use.

20. An immunohistochemical method of detecting breast cancer in a cell, tissue, or blood sample collected from a human subject comprising the steps of:
  a) obtaining a tissue, cell, or blood sample from a human subject;
  b) contacting said sample with the antibody or antibody fragment of claim 1;
  c) quantitatively determining whether the antibody specifically binds to said sample;
  d) comparing the level of specific binding in the sample to a control, wherein binding at a level that is lower than in the control indicates the presence of breast cancer.

21. A method of treating cancer with an anti-ALPHA-ACTININ-4 antibody or antibody fragment comprising obtaining a tissue, cell, or blood sample from a human subject; applying the antibody or antibody fragment of claim 1 to the sample; quantitatively determining the level of specific binding of the antibody as compared to a control; and providing an anti-ALPHA-ACTININ-4 antibody treatment to said patient if the antibody or antibody fragment specifically binds at a level that is less than the level of binding in the control.

22. A prognostic method for determining the severity of disease in a patient diagnosed with or suspected of having breast cancer comprising:
  a) obtaining a cell or tissue sample from a human subject diagnosed with or suspected of having breast cancer;
  b) contacting the sample with the antibody or antibody fragment of claim 1;
  c) detecting the antibody;
  d) scoring the detection pathologically, wherein a pathology score of 0 indicates no staining in the sample, a score of 1+ indicates weak staining in the sample; a score of 2+ indicates intermediate staining in the sample; and a score of 3+ indicates strong staining in the sample; and
e) providing a prognosis to the patient, wherein the pathology score inversely correlates with the severity of disease.

* * * * *